United States Patent
Ignon et al.

(10) Patent No.: US 11,744,999 B2
(45) Date of Patent: Sep. 5, 2023

(54) DEVICES AND METHODS FOR TREATING THE SKIN

(71) Applicant: HYDRAFACIAL LLC, Long Beach, CA (US)

(72) Inventors: Roger Ignon, Redondo Beach, CA (US); Ed F. Nicolas, Signal Hill, CA (US)

(73) Assignee: Hydra Facial LLC, Long Beach, CA (US)

( * ) Notice: Subject to any disclaimer, the term of this patent is extended or adjusted under 35 U.S.C. 154(b) by 0 days.

(21) Appl. No.: 17/164,580

(22) Filed: Feb. 1, 2021

(65) Prior Publication Data
US 2021/0154453 A1     May 27, 2021

Related U.S. Application Data

(63) Continuation of application No. 16/040,397, filed on Jul. 19, 2018, which is a continuation of application
(Continued)

(51) Int. Cl.
*A61M 35/00* (2006.01)
*A45D 34/04* (2006.01)
(Continued)

(52) U.S. Cl.
CPC ........... *A61M 35/003* (2013.01); *A45D 34/04* (2013.01); *A45D 34/041* (2013.01);
(Continued)

(58) Field of Classification Search
CPC ... A61M 35/003; A61M 35/006; A61B 17/54; A61B 17/545
See application file for complete search history.

(56) References Cited

U.S. PATENT DOCUMENTS 1,651,585 A   12/1927   Clair
2,608,032 A   8/1952    Garver
(Continued)

FOREIGN PATENT DOCUMENTS

AT   400 305     12/1995
AU   1 014 299   5/1999
(Continued)

OTHER PUBLICATIONS

Cox III et al., Decreased Splatter in Dermabrasion, Arch Facial Plastic Surgery, Jan.-Mar. 2000, vol. 2, pp. 23-26.
(Continued)

*Primary Examiner* — Catharine L Anderson
*Assistant Examiner* — Arjuna P Chatrathi
(74) *Attorney, Agent, or Firm* — Knobbe, Martens, Olson & Bear, LLP

(57) ABSTRACT

According to some embodiments, a skin treatment assembly comprises a handpiece comprising a distal end, the handpiece comprising a recess or cavity configured to receive a cartridge or other fluid container, a tip configured to be positioned along the distal end of the handpiece, the tip being configured to contact a skin surface of a subject during use, and at least one rollerball configured to extend to or near the tip, wherein the rollerball is configured to be in fluid communication with an interior of a cartridge or other fluid container secured to the handpiece, wherein the at least one rollerball is configured to contact the skin surface of the subject during use and to facilitate the delivery of fluids to said skin surface as the rollerball is moved relative to said skin surface.

20 Claims, 19 Drawing Sheets

Related U.S. Application Data

No. 15/354,754, filed on Nov. 17, 2016, now Pat. No. 10,035,007, which is a continuation of application No. 14/998,375, filed on Dec. 23, 2015, now Pat. No. 9,498,610.

(60) Provisional application No. 62/235,479, filed on Sep. 30, 2015, provisional application No. 62/096,493, filed on Dec. 23, 2014.

(51) Int. Cl.
*A61B 17/54* (2006.01)
*A61M 37/00* (2006.01)
*A45D 34/00* (2006.01)
*A61B 17/00* (2006.01)
*A61B 17/3205* (2006.01)
*A61B 17/32* (2006.01)

(52) U.S. Cl.
CPC .......... *A61B 17/3205* (2013.01); *A61B 17/54* (2013.01); *A61B 17/545* (2013.01); *A61M 35/006* (2013.01); *A61M 37/00* (2013.01); *A45D 2034/005* (2013.01); *A61B 2017/00747* (2013.01); *A61B 2017/00761* (2013.01); *A61B 2017/320004* (2013.01); *A61B 2217/005* (2013.01); *A61M 2210/04* (2013.01)

(56) References Cited

U.S. PATENT DOCUMENTS

| | | |
|---|---|---|
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,560,100 A * | 2/1971 | Spatz .................. A45D 34/041 401/180 |
| 3,574,239 A | 4/1971 | Sollerud |
| 3,715,838 A | 2/1973 | Young et al. |
| 3,865,352 A | 2/1975 | Nelson et al. |
| 3,866,264 A | 2/1975 | Engquist |
| 3,930,598 A | 1/1976 | Slagle |
| 3,948,265 A | 4/1976 | Al Ani |
| 3,964,212 A | 6/1976 | Karden |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| 4,216,233 A | 8/1980 | Stein |
| 4,225,254 A | 9/1980 | Holberg et al. |
| D260,176 S | 8/1981 | Boschetti et al. |
| 4,289,158 A | 9/1981 | Nehring |
| 4,299,219 A | 11/1981 | Norris, Jr. |
| 4,342,522 A | 8/1982 | Mackles |
| 4,378,804 A | 4/1983 | Cortese |
| 4,500,222 A * | 2/1985 | Clading-Boel ........ B43K 7/105 401/209 |
| 4,560,373 A | 12/1985 | Sugino et al. |
| 4,646,480 A | 3/1987 | Williams |
| 4,646,482 A | 3/1987 | Chitjian |
| 4,655,743 A | 4/1987 | Hyde |
| 4,676,749 A | 6/1987 | Mabille |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,875,287 A | 10/1989 | Creasy et al. |
| 4,886,078 A | 12/1989 | Shiffman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| 4,940,350 A | 7/1990 | Kim |
| 4,957,747 A | 9/1990 | Stiefel |
| 5,006,004 A | 4/1991 | Dirksing et al. |
| 5,006,339 A | 4/1991 | Bargery et al. |
| 5,012,797 A | 5/1991 | Clarke |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,222,956 A | 6/1993 | Waldron |
| 5,242,433 A | 9/1993 | Smith et al. |
| 5,254,109 A | 10/1993 | Smith et al. |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Clarke |
| 5,658,583 A | 8/1997 | Zhang et al. |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore et al. |
| 5,813,416 A | 9/1998 | Rudolph |
| 5,817,050 A | 10/1998 | Klein |
| 5,834,510 A | 11/1998 | Yu et al. |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,882,201 A | 3/1999 | Salem |
| 5,885,260 A | 3/1999 | Mehl, Sr. et al. |
| 5,908,401 A | 6/1999 | Henley |
| 5,919,152 A | 7/1999 | Zygmont |
| 5,919,479 A | 7/1999 | Zhang et al. |
| 5,954,730 A | 9/1999 | Bernabei |
| 5,971,999 A | 10/1999 | Naldoni |

(56) References Cited

U.S. PATENT DOCUMENTS

| | | |
|---|---|---|
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,039,745 A | 3/2000 | Di Fiore et al. |
| 6,042,552 A | 3/2000 | Cornier |
| 6,080,165 A | 6/2000 | DeJacma |
| 6,080,166 A | 6/2000 | McEwen et al. |
| 6,090,085 A | 7/2000 | Mehl, Sr. et al. |
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Park et al. |
| 6,176,198 B1 | 1/2001 | Kao et al. |
| 6,183,451 B1 | 2/2001 | Mehl, Sr. et al. |
| 6,183,483 B1 | 2/2001 | Chang |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,245,347 B1 | 6/2001 | Zhang et al. |
| 6,264,666 B1 | 7/2001 | Coleman et al. |
| 6,277,116 B1 | 8/2001 | Utely et al. |
| 6,277,128 B1 | 8/2001 | Muldner |
| 6,283,978 B1 | 9/2001 | Cheski et al. |
| 6,284,266 B1 | 9/2001 | Zhang et al. |
| 6,299,620 B1 * | 10/2001 | Shadduck .............. A61B 17/54 604/289 |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bernabei et al. |
| 6,332,886 B1 | 12/2001 | Green et al. |
| 6,355,054 B1 | 3/2002 | Neuberger |
| 6,368,333 B2 | 4/2002 | Bernabei et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,471,712 B2 | 10/2002 | Burres |
| 6,477,410 B1 | 11/2002 | Henley et al. |
| 6,482,212 B1 | 11/2002 | Bernabei et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,508,813 B1 | 1/2003 | Altshuler |
| 6,511,486 B2 | 1/2003 | Mercier et al. |
| 6,514,262 B1 | 2/2003 | Di Fiore et al. |
| 6,520,931 B2 | 2/2003 | Suh |
| 6,527,783 B1 | 3/2003 | Ignon |
| 6,535,761 B2 | 3/2003 | Bernabei |
| 6,537,242 B1 | 3/2003 | Palmer |
| 6,540,757 B1 | 4/2003 | Hruska et al. |
| 6,546,281 B1 | 4/2003 | Zhang et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,582,442 B2 | 6/2003 | Simon et al. |
| 6,589,218 B2 | 7/2003 | Garcia |
| 6,592,595 B1 | 7/2003 | Mallett et al. |
| 6,626,445 B2 | 9/2003 | Murphy et al. |
| 6,629,927 B1 | 10/2003 | Mesaros et al. |
| 6,629,983 B1 | 10/2003 | Ignon |
| 6,635,035 B1 | 10/2003 | Marasco et al. |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| D486,915 S | 2/2004 | Warschewske et al. |
| 6,685,853 B1 | 2/2004 | Angelopoulous et al. |
| 6,687,537 B2 | 2/2004 | Bernabei |
| 6,689,380 B1 | 2/2004 | Marchitto et al. |
| 6,695,853 B2 | 2/2004 | Karasiuk |
| 6,726,673 B1 | 4/2004 | Zhang et al. |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| 6,780,426 B2 | 8/2004 | Zhang et al. |
| D496,101 S | 9/2004 | Davison |
| 6,800,083 B2 | 10/2004 | Hiblar et al. |
| 6,800,849 B2 | 10/2004 | Staats |
| 6,869,611 B1 | 3/2005 | Kligman et al. |
| 6,905,487 B2 | 6/2005 | Zimmerman |
| 6,911,031 B2 | 6/2005 | Muldner |
| 6,926,681 B1 | 8/2005 | Ramey et al. |
| 6,938,805 B2 | 9/2005 | Brincat |
| 6,942,649 B2 | 9/2005 | Ignon et al. |
| 6,960,206 B2 | 11/2005 | Keane |
| 6,980,448 B2 | 12/2005 | Foss et al. |
| 7,001,355 B2 | 2/2006 | Nunomura et al. |
| 7,004,933 B2 | 2/2006 | McDaniel |
| D517,699 S | 3/2006 | Lansohn |
| 7,044,938 B2 | 5/2006 | La Bianco et al. |
| 7,051,907 B2 | 5/2006 | Brincat |
| 7,052,503 B2 | 5/2006 | Bernabei |
| D522,360 S | 6/2006 | Caserta et al. |
| 7,069,073 B2 | 6/2006 | Henley et al. |
| 7,070,488 B2 | 7/2006 | Suissa et al. |
| 7,083,580 B2 | 8/2006 | Bernabei |
| 7,087,036 B2 | 8/2006 | Busby et al. |
| 7,087,063 B2 | 8/2006 | Carson et al. |
| 7,094,252 B2 | 8/2006 | Koop |
| 7,115,275 B2 | 10/2006 | Clarot et al. |
| 7,135,011 B2 | 11/2006 | Powers et al. |
| 7,153,311 B2 | 12/2006 | Chung |
| 7,166,086 B2 | 1/2007 | Haider et al. |
| 7,172,572 B2 | 2/2007 | Diamond et al. |
| 7,197,359 B1 | 3/2007 | Tokudome et al. |
| 7,198,623 B2 | 4/2007 | Fischer et al. |
| 7,232,444 B2 | 6/2007 | Chang |
| 7,241,208 B2 | 7/2007 | Suissa et al. |
| D553,005 S | 10/2007 | Py et al. |
| 7,276,051 B1 | 10/2007 | Henley et al. |
| 7,293,930 B2 * | 11/2007 | Chuang ................ A45D 40/261 401/214 |
| 7,314,326 B2 | 1/2008 | Rosenberg |
| 7,316,657 B2 | 1/2008 | Kleinhenz et al. |
| 7,316,671 B2 | 1/2008 | Lastovich et al. |
| 7,318,828 B1 | 1/2008 | Revivo |
| 7,320,691 B2 | 1/2008 | Pilcher et al. |
| 7,320,801 B2 | 1/2008 | Kelly |
| 7,354,423 B2 | 4/2008 | Zelickson et al. |
| 7,364,565 B2 | 4/2008 | Freeman |
| 7,384,405 B2 | 6/2008 | Rhoades |
| 7,422,567 B2 | 9/2008 | Lastovich et al. |
| 7,427,273 B2 | 9/2008 | Mitsui |
| 7,440,798 B2 | 10/2008 | Redding, Jr. |
| 7,458,944 B2 | 12/2008 | Liste et al. |
| D584,151 S | 1/2009 | Murphy |
| 7,476,205 B2 | 1/2009 | Erdmann |
| 7,477,938 B2 | 1/2009 | Sun et al. |
| 7,482,314 B2 | 1/2009 | Grimes et al. |

(56) References Cited

U.S. PATENT DOCUMENTS

| | | |
|---|---|---|
| 7,485,125 B2 | 2/2009 | Sjostrom |
| 7,489,989 B2 | 2/2009 | Sukhanov et al. |
| 7,507,228 B2 | 3/2009 | Sun et al. |
| 7,582,067 B2 | 9/2009 | Van Acker |
| 7,597,900 B2 | 10/2009 | Zimmer et al. |
| 7,597,901 B2 | 10/2009 | Clarot et al. |
| 7,658,742 B2 | 2/2010 | Karasiuk |
| 7,678,120 B2 | 3/2010 | Shadduck |
| 7,744,582 B2 | 6/2010 | Sadowski et al. |
| 7,789,886 B2 | 9/2010 | Shadduck |
| 7,837,695 B2 | 11/2010 | Hart et al. |
| 7,857,806 B2 | 12/2010 | Karpowicz et al. |
| 7,901,373 B2 | 3/2011 | Tavger |
| 7,951,156 B2 | 5/2011 | Karasiuk |
| 7,993,333 B2 | 8/2011 | Oral et al. |
| 8,025,669 B1 | 9/2011 | David et al. |
| RE42,960 E | 11/2011 | Waldron |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| D664,254 S | 7/2012 | Yokoyama et al. |
| 8,221,437 B2 | 7/2012 | Waldron et al. |
| 8,231,292 B2 | 7/2012 | Rabe et al. |
| 8,236,008 B2 | 8/2012 | Boone, III et al. |
| 8,277,287 B2 | 10/2012 | Hart |
| 8,337,513 B2 | 12/2012 | Shadduck |
| 8,343,116 B2 | 1/2013 | Ignon et al. |
| D678,783 S | 3/2013 | Wilcox et al. |
| 8,475,507 B2 | 7/2013 | Dewey et al. |
| 8,478,396 B2 | 7/2013 | Tsao et al. |
| 8,535,299 B2 | 9/2013 | Giovannoli |
| 8,545,489 B2 | 10/2013 | Giovannoli |
| 8,562,626 B2 | 10/2013 | Sabir et al. |
| 8,573,874 B2 | 11/2013 | Neuner |
| 8,579,916 B2 | 11/2013 | Cheney |
| 8,721,662 B2 | 5/2014 | Karasiuk |
| D709,617 S | 7/2014 | Iliesco de Grimaldi et al. |
| 8,814,836 B2 | 8/2014 | Ignon et al. |
| 8,858,570 B2 | 10/2014 | Chang |
| 8,939,669 B2 | 1/2015 | Le et al. |
| D722,172 S | 2/2015 | Amemiya et al. |
| 8,945,104 B2 | 2/2015 | Boone, III et al. |
| 9,044,582 B2 | 6/2015 | Chang et al. |
| 9,050,133 B1 | 6/2015 | Boone, III et al. |
| 9,056,193 B2 | 6/2015 | Ignon et al. |
| 9,072,533 B2 | 7/2015 | Liu et al. |
| D743,558 S | 11/2015 | Kim et al. |
| 9,186,490 B2 | 11/2015 | Chang et al. |
| 9,227,044 B2 | 1/2016 | Bansal et al. |
| 9,271,755 B2 | 3/2016 | Luzon et al. |
| 9,468,464 B2 | 10/2016 | Shadduck |
| 9,474,886 B2 | 10/2016 | Ignon et al. |
| 9,486,615 B2 | 11/2016 | Ignon et al. |
| 9,498,610 B2 | 11/2016 | Ignon et al. |
| 9,517,085 B2 | 12/2016 | Karasiuk |
| 9,550,052 B2 | 1/2017 | Ignon et al. |
| 9,566,088 B2 | 2/2017 | Ignon et al. |
| 9,597,527 B2 | 3/2017 | Buchholz et al. |
| D787,054 S | 5/2017 | Rini et al. |
| 9,636,521 B2 | 5/2017 | Isserow et al. |
| 9,636,522 B2 | 5/2017 | Oversluizen et al. |
| 9,642,997 B2 | 5/2017 | Ignon et al. |
| 9,662,482 B2 | 5/2017 | Ignon et al. |
| 9,669,233 B2 | 6/2017 | Quisenberry et al. |
| 9,675,817 B2 | 6/2017 | Isserow et al. |
| 9,700,684 B2 | 7/2017 | Vlodaver et al. |
| 9,731,053 B2 | 8/2017 | Alai |
| 9,775,645 B2 | 10/2017 | Boone, III |
| 9,775,646 B2 | 10/2017 | Shadduck |
| 9,775,976 B2 | 10/2017 | Grez |
| 9,814,485 B2 | 11/2017 | Pratt et al. |
| 9,814,647 B2 | 11/2017 | Ajiki |
| 9,814,868 B2 | 11/2017 | Ignon et al. |
| 9,833,261 B2 | 12/2017 | Boone, III et al. |
| 9,861,442 B2 | 1/2018 | Tankovich et al. |
| D811,381 S | 2/2018 | Morohoshi et al. |
| 9,918,727 B1 | 3/2018 | Boone, III et al. |
| 9,949,552 B2 | 4/2018 | Rabe et al. |
| 9,950,147 B2 | 4/2018 | Mehta |
| 9,955,769 B2 | 5/2018 | Rabe et al. |
| 9,968,800 B2 | 5/2018 | Anderson et al. |
| 10,004,919 B2 | 6/2018 | Lemmens et al. |
| D822,845 S | 7/2018 | Shimobayashi et al. |
| 10,010,445 B2 | 7/2018 | Isserow et al. |
| 10,022,289 B2 | 7/2018 | Ajiki et al. |
| 10,035,007 B2 | 7/2018 | Ignon et al. |
| D825,763 S | 8/2018 | Lim et al. |
| 10,052,467 B2 | 8/2018 | Bansal et al. |
| 10,076,354 B2 | 9/2018 | Knowlton |
| 10,076,646 B2 | 9/2018 | Casasanta, III et al. |
| 10,080,581 B2 | 9/2018 | Knowlton |
| 10,092,478 B1 | 10/2018 | Amit |
| 10,130,390 B1 | 11/2018 | Hart et al. |
| 10,130,827 B2 | 11/2018 | Buchholz et al. |
| D836,781 S | 12/2018 | Meurer et al. |
| 10,172,644 B2 | 1/2019 | Ignon et al. |
| 10,179,229 B2 | 1/2019 | Ignon et al. |
| 10,188,193 B2 | 1/2019 | Rabe et al. |
| 10,206,743 B2 | 2/2019 | Tankovich et al. |
| 10,207,034 B2 | 2/2019 | Collins |
| 10,220,122 B2 | 3/2019 | Clark, III et al. |
| 10,238,812 B2 | 3/2019 | Ignon |
| 10,251,675 B2 | 4/2019 | Ignon et al. |
| 10,272,258 B2 | 4/2019 | Quisenberry et al. |
| D851,759 S | 6/2019 | Jones et al. |
| 10,308,378 B2 | 6/2019 | Goodwin et al. |
| 10,314,378 B2 | 6/2019 | Rabe et al. |
| 10,321,948 B2 | 6/2019 | Knowlton |
| D852,962 S | 7/2019 | Chang |
| 10,335,191 B2 | 7/2019 | Knowlton |
| 10,357,641 B2 | 7/2019 | Ignon et al. |
| 10,357,642 B2 | 7/2019 | Ignon et al. |
| 10,334,933 B2 | 8/2019 | Rosario et al. |
| 10,369,073 B2 | 8/2019 | Rosario et al. |
| D861,913 S | 10/2019 | Stamm et al. |
| 10,456,321 B2 | 10/2019 | Shadduck |
| 10,456,567 B2 | 10/2019 | Streeter |
| D867,587 S | 11/2019 | Holtz |
| 10,485,983 B1 | 11/2019 | Boone, III et al. |
| D868,981 S | 12/2019 | Salamon et al. |
| D873,430 S | 1/2020 | Accolla |
| 10,524,835 B2 | 1/2020 | Shadduck et al. |
| 10,556,096 B2 | 2/2020 | Ignon et al. |
| 10,556,097 B2 | 2/2020 | Ignon et al. |
| 10,583,037 B2 | 3/2020 | Isserow et al. |
| D887,571 S | 6/2020 | Liu |
| 10,667,985 B2 | 6/2020 | Decaux et al. |
| 10,716,924 B2 | 7/2020 | Knowlton |
| D893,024 S | 8/2020 | Whiteside |
| 10,737,080 B2 | 8/2020 | Patterson |
| 10,758,261 B2 | 9/2020 | Richardson |
| 10,772,658 B2 | 9/2020 | Knowlton |
| 10,792,382 B2 | 10/2020 | Rafko |
| 10,835,287 B2 | 11/2020 | Shadduck et al. |
| 10,856,900 B2 | 12/2020 | Knowlton |
| 10,874,579 B1 | 12/2020 | Rembert |
| 10,912,428 B2 | 2/2021 | Daffer |
| 10,918,190 B2 | 2/2021 | Laudati |
| 10,946,191 B2 | 3/2021 | Cazares Delgadillo |
| 10,952,907 B1 | 3/2021 | Carver |
| 10,993,743 B2 | 5/2021 | Ignon et al. |
| 11,020,577 B2 | 6/2021 | Ignon et al. |
| 11,045,661 B2 | 6/2021 | Oversluizen et al. |
| D927,008 S | 8/2021 | Rappaport |
| D928,977 S | 8/2021 | Dijkstra |
| 11,141,761 B2 | 10/2021 | Connelly et al. |
| 11,154,723 B2 | 10/2021 | Lee |
| 11,202,657 B2 | 12/2021 | Ignon et al. |
| 11,213,321 B2 | 1/2022 | Ignon et al. |
| 11,224,728 B2 | 1/2022 | Ignon et al. |
| 11,241,357 B2 | 2/2022 | Ignon et al. |
| 11,291,474 B2 | 4/2022 | Nicolas et al. |

(56) References Cited

U.S. PATENT DOCUMENTS

| | | | |
|---|---|---|---|
| 11,351,063 B2 | 6/2022 | Locke et al. | |
| 11,446,477 B2 | 9/2022 | Ignon | |
| 11,452,852 B2 | 9/2022 | Quan et al. | |
| 11,504,148 B2 | 11/2022 | Friend | |
| 11,517,350 B2 | 12/2022 | Ignon et al. | |
| 11,547,840 B2 | 1/2023 | Ignon et al. | |
| 2001/0023351 A1 | 9/2001 | Eilers | |
| 2001/0037118 A1* | 11/2001 | Shadduck | A61B 17/545 606/131 |
| 2001/0049511 A1 | 12/2001 | Coleman et al. | |
| 2002/0016601 A1 | 2/2002 | Shadduck | |
| 2002/0041891 A1 | 4/2002 | Cheski | |
| 2002/0058952 A1 | 5/2002 | Weber et al. | |
| 2002/0099356 A1 | 7/2002 | Unger et al. | |
| 2002/0107527 A1 | 8/2002 | Burres | |
| 2002/0128663 A1 | 9/2002 | Mercier et al. | |
| 2002/0133110 A1 | 9/2002 | Citow | |
| 2002/0133176 A1 | 9/2002 | Parkin et al. | |
| 2002/0151826 A1 | 10/2002 | Ramey et al. | |
| 2002/0151908 A1 | 10/2002 | Mallett, Sr. et al. | |
| 2002/0162863 A1* | 11/2002 | Brincat | B65D 11/04 222/568 |
| 2002/0188261 A1 | 12/2002 | Hruska | |
| 2002/0198488 A1 | 12/2002 | Yao | |
| 2003/0012415 A1 | 1/2003 | Cossel | |
| 2003/0018252 A1 | 1/2003 | Duchon et al. | |
| 2003/0060834 A1 | 3/2003 | Muldner | |
| 2003/0093040 A1 | 5/2003 | Mikszta et al. | |
| 2003/0093089 A1 | 5/2003 | Greenberg | |
| 2003/0097139 A1 | 5/2003 | Karasiuk | |
| 2003/0167032 A1* | 9/2003 | Ignon | A61B 17/545 604/19 |
| 2003/0187462 A1 | 10/2003 | Chang | |
| 2003/0208159 A1 | 11/2003 | Ignon et al. | |
| 2003/0212127 A1 | 11/2003 | Glassman et al. | |
| 2003/0212415 A1 | 11/2003 | Karasiuk | |
| 2004/0010222 A1 | 1/2004 | Nunomura et al. | |
| 2004/0010269 A1 | 1/2004 | Grimes et al. | |
| 2004/0015139 A1 | 1/2004 | La Bianco | |
| 2004/0087972 A1 | 5/2004 | Mulholland et al. | |
| 2004/0092895 A1 | 5/2004 | Harmon | |
| 2004/0092959 A1 | 5/2004 | Bernaz | |
| 2004/0097967 A1 | 5/2004 | Ignon | |
| 2004/0122447 A1 | 6/2004 | Harmon et al. | |
| 2004/0127914 A1 | 7/2004 | Chung | |
| 2004/0138680 A1 | 7/2004 | Twitchell et al. | |
| 2004/0143274 A1 | 7/2004 | Shadduck | |
| 2004/0162565 A1 | 8/2004 | Carson et al. | |
| 2004/0166172 A1 | 8/2004 | Rosati et al. | |
| 2004/0210280 A1 | 10/2004 | Liedtke | |
| 2004/0219179 A1 | 11/2004 | McDaniel | |
| 2004/0229295 A1 | 11/2004 | Marchitto et al. | |
| 2004/0236291 A1 | 11/2004 | Zelickson et al. | |
| 2004/0236375 A1 | 11/2004 | Redding, Jr. | |
| 2004/0243149 A1 | 12/2004 | Lee, Jr. | |
| 2004/0254587 A1 | 12/2004 | Park | |
| 2004/0267285 A1 | 12/2004 | Chang | |
| 2005/0037034 A1 | 2/2005 | Rhoades | |
| 2005/0038377 A1 | 2/2005 | Redding, Jr. | |
| 2005/0038448 A1 | 2/2005 | Chung | |
| 2005/0059940 A1 | 3/2005 | Weber et al. | |
| 2005/0065461 A1 | 3/2005 | Redding, Jr. | |
| 2005/0070977 A1 | 3/2005 | Molina | |
| 2005/0075599 A1 | 4/2005 | Redding, Jr. | |
| 2005/0080465 A1 | 4/2005 | Zelickson et al. | |
| 2005/0084509 A1 | 4/2005 | Bernstein | |
| 2005/0148958 A1 | 7/2005 | Rucinski | |
| 2005/0203111 A1 | 9/2005 | David | |
| 2005/0209611 A1 | 9/2005 | Greenberg | |
| 2005/0283176 A1 | 12/2005 | Law | |
| 2006/0002960 A1 | 1/2006 | Zoeteweij et al. | |
| 2006/0015059 A1 | 1/2006 | Redding, Jr. | |
| 2006/0058714 A1 | 3/2006 | Rhoades | |
| 2006/0100567 A1 | 5/2006 | Marchitto et al. | |
| 2006/0116674 A1 | 6/2006 | Goble et al. | |
| 2006/0161178 A1 | 7/2006 | Lee | |
| 2006/0189964 A1 | 8/2006 | Anderson | |
| 2006/0191562 A1 | 8/2006 | Numomura | |
| 2006/0200099 A1 | 9/2006 | La Bianco et al. | |
| 2006/0200172 A1 | 9/2006 | Shadduck | |
| 2006/0200173 A1 | 9/2006 | Shadduck | |
| 2006/0212025 A1 | 9/2006 | McDaniel | |
| 2006/0212029 A1 | 9/2006 | Villacampa et al. | |
| 2006/0222445 A1 | 10/2006 | Chuang | |
| 2006/0253078 A1 | 11/2006 | Wu et al. | |
| 2006/0253079 A1 | 11/2006 | McDonough et al. | |
| 2006/0253125 A1 | 11/2006 | Ignon | |
| 2006/0264893 A1 | 11/2006 | Sage, Jr. et al. | |
| 2006/0269580 A1 | 11/2006 | Cole et al. | |
| 2006/0278661 A1 | 12/2006 | Cooper et al. | |
| 2007/0005078 A1 | 1/2007 | Hart et al. | |
| 2007/0020321 A1 | 1/2007 | Redding et al. | |
| 2007/0043382 A1 | 2/2007 | Cheney | |
| 2007/0049901 A1 | 3/2007 | Wu et al. | |
| 2007/0065515 A1 | 3/2007 | Key | |
| 2007/0073327 A1 | 3/2007 | Giovannoli | |
| 2007/0088371 A1 | 4/2007 | Karasiuk | |
| 2007/0093694 A1* | 4/2007 | Fassuliotis | A61B 17/02 600/205 |
| 2007/0123808 A1 | 5/2007 | Rhoades | |
| 2007/0139630 A1 | 6/2007 | Kiernan et al. | |
| 2007/0149991 A1 | 6/2007 | Mulholland | |
| 2007/0154502 A1 | 7/2007 | Hattendorf et al. | |
| 2007/0156124 A1 | 7/2007 | Ignon et al. | |
| 2007/0178121 A1 | 8/2007 | First et al. | |
| 2007/0198031 A1 | 8/2007 | Kellogg | |
| 2007/0208353 A1 | 9/2007 | Shadduck | |
| 2007/0239173 A1 | 10/2007 | Khalaj | |
| 2007/0270738 A1 | 11/2007 | Wu et al. | |
| 2008/0009802 A1 | 1/2008 | Lambino et al. | |
| 2008/0027328 A1 | 1/2008 | Klopotek et al. | |
| 2008/0091126 A1 | 4/2008 | Greenburg | |
| 2008/0091179 A1 | 4/2008 | Durkin et al. | |
| 2008/0103563 A1 | 5/2008 | Powell | |
| 2008/0119781 A1 | 5/2008 | King | |
| 2008/0132914 A1 | 6/2008 | Bossard et al. | |
| 2008/0139974 A1 | 6/2008 | Da Silva | |
| 2008/0154161 A1 | 6/2008 | Abbott | |
| 2008/0154183 A1 | 6/2008 | Baker et al. | |
| 2008/0161799 A1 | 7/2008 | Stangenes et al. | |
| 2008/0188840 A1 | 8/2008 | Johnson et al. | |
| 2008/0193493 A1 | 8/2008 | Rhoades | |
| 2008/0200861 A1 | 8/2008 | Shalev et al. | |
| 2008/0200863 A1 | 8/2008 | Chomas et al. | |
| 2008/0208146 A1 | 8/2008 | Brandwein et al. | |
| 2008/0214987 A1 | 9/2008 | Xu | |
| 2008/0215068 A1 | 9/2008 | Hart et al. | |
| 2008/0221548 A1 | 9/2008 | Danenberg et al. | |
| 2008/0243039 A1 | 10/2008 | Rhoades | |
| 2008/0287864 A1 | 11/2008 | Rosenberg | |
| 2008/0300529 A1 | 12/2008 | Reinstein | |
| 2008/0300552 A1 | 12/2008 | Cichocki et al. | |
| 2009/0048557 A1 | 2/2009 | Yeshurun et al. | |
| 2009/0053390 A1 | 2/2009 | Sakou et al. | |
| 2009/0062815 A1 | 3/2009 | Karasiuk et al. | |
| 2009/0099091 A1 | 4/2009 | Hantash | |
| 2009/0099093 A1 | 4/2009 | Hantash | |
| 2009/0124985 A1 | 5/2009 | Hasenoehrl et al. | |
| 2009/0138026 A1 | 5/2009 | Wu | |
| 2009/0177171 A1 | 7/2009 | Ignon et al. | |
| 2009/0192442 A1* | 7/2009 | Ignon | A61B 17/54 604/22 |
| 2009/0222023 A1 | 9/2009 | Boone, III et al. | |
| 2009/0254014 A1 | 10/2009 | Son | |
| 2010/0023003 A1 | 1/2010 | Mulholland | |
| 2010/0036298 A1 | 2/2010 | Foster | |
| 2010/0045427 A1 | 2/2010 | Boone, III et al. | |
| 2010/0048980 A1 | 2/2010 | De Jong et al. | |
| 2010/0049177 A1 | 2/2010 | Boone, III et al. | |
| 2010/0049210 A1 | 2/2010 | Boone, III et al. | |
| 2010/0056847 A1 | 3/2010 | De Jong et al. | |
| 2010/0217357 A1 | 8/2010 | Da Silva | |
| 2010/0305495 A1 | 12/2010 | Anderson et al. | |
| 2011/0054490 A1 | 3/2011 | Hart | |

(56) References Cited

U.S. PATENT DOCUMENTS

| | | |
|---|---|---|
| 2011/0066162 A1 | 3/2011 | Cohen |
| 2011/0082415 A1* | 4/2011 | Ignon .............. A61M 37/00 604/22 |
| 2011/0264028 A1 | 10/2011 | Ramdas et al. |
| 2011/0295273 A1* | 12/2011 | Waldron ............ A61B 17/54 606/131 |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2012/0289885 A1 | 11/2012 | Cottrell et al. |
| 2012/0302929 A1 | 11/2012 | Tkachenko |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144207 A1 | 6/2013 | Gonon |
| 2013/0144280 A1 | 6/2013 | Eckhouse et al. |
| 2013/0158547 A1 | 6/2013 | David |
| 2013/0226269 A1 | 8/2013 | Eckhouse et al. |
| 2013/0261534 A1 | 10/2013 | Niezgoda et al. |
| 2014/0031801 A1 | 1/2014 | Giovannoli |
| 2014/0079686 A1 | 3/2014 | Barman et al. |
| 2014/0081251 A1 | 3/2014 | Giovannoli |
| 2014/0234004 A1 | 8/2014 | Thorpe et al. |
| 2014/0243589 A1 | 8/2014 | Rowan |
| 2014/0316492 A1 | 10/2014 | Min et al. |
| 2014/0343481 A1 | 11/2014 | Ignon |
| 2014/0343574 A1 | 11/2014 | Ignon et al. |
| 2014/0378887 A1 | 12/2014 | Chang et al. |
| 2015/0032047 A1 | 1/2015 | Ignon et al. |
| 2015/0039060 A1 | 2/2015 | Paulussen et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272632 A1 | 10/2015 | Seelig |
| 2015/0290442 A1 | 10/2015 | Ignon et al. |
| 2016/0015962 A1 | 1/2016 | Maragheh et al. |
| 2016/0018100 A1 | 1/2016 | Batt et al. |
| 2016/0038183 A1 | 2/2016 | Ignon et al. |
| 2016/0175609 A1 | 6/2016 | Dye et al. |
| 2016/0235257 A1 | 8/2016 | Daffer |
| 2016/0250415 A1 | 9/2016 | Yagi et al. |
| 2017/0036002 A1 | 2/2017 | Ignon et al. |
| 2017/0043150 A1 | 2/2017 | Kim |
| 2017/0065801 A1 | 3/2017 | Ignon et al. |
| 2017/0157419 A1 | 6/2017 | Jeong |
| 2017/0196759 A1 | 7/2017 | Palomaki et al. |
| 2017/0209894 A1 | 7/2017 | Sporrer |
| 2017/0291007 A1 | 10/2017 | Dubey et al. |
| 2017/0340356 A1 | 11/2017 | Presser et al. |
| 2018/0140329 A1 | 5/2018 | Beijens et al. |
| 2018/0185675 A1 | 7/2018 | Kern et al. |
| 2018/0318568 A1 | 11/2018 | Ignon et al. |
| 2018/0326191 A1 | 11/2018 | Bansal et al. |
| 2019/0070069 A1 | 3/2019 | Gertner et al. |
| 2019/0133642 A1 | 5/2019 | Ignon et al. |
| 2019/0143089 A1 | 5/2019 | Ignon et al. |
| 2019/0151637 A1 | 5/2019 | Groop et al. |
| 2019/0168016 A1 | 6/2019 | Anderson et al. |
| 2019/0209859 A1 | 7/2019 | Quisenberry et al. |
| 2019/0223914 A1 | 7/2019 | Ignon et al. |
| 2019/0240502 A1 | 8/2019 | Anderson et al. |
| 2019/0336740 A1 | 11/2019 | Ignon et al. |
| 2019/0366067 A1 | 12/2019 | Ginggen et al. |
| 2020/0009007 A1 | 1/2020 | Shadduck |
| 2020/0016342 A1 | 1/2020 | Ignon |
| 2020/0030627 A1 | 1/2020 | Eltorai et al. |
| 2020/0101312 A1 | 4/2020 | Pai et al. |
| 2020/0114116 A1 | 4/2020 | Dubey et al. |
| 2020/0171288 A1 | 6/2020 | Ignon et al. |
| 2020/0171289 A1 | 6/2020 | Ignon et al. |
| 2020/0179220 A1 | 6/2020 | Jablow |
| 2020/0289161 A1 | 9/2020 | Scooros |
| 2020/0306555 A1 | 10/2020 | Ebbesson |
| 2020/0316270 A1 | 10/2020 | Dijkstra et al. |
| 2020/0330754 A1 | 10/2020 | Kim et al. |
| 2020/0338586 A1 | 10/2020 | Park |
| 2020/0390468 A1 | 12/2020 | Alexander |
| 2021/0085367 A1 | 3/2021 | Shadduck et al. |
| 2021/0145479 A1 | 5/2021 | Ignon et al. |
| 2021/0145480 A1 | 5/2021 | Ignon et al. |
| 2021/0145481 A1 | 5/2021 | Ignon et al. |
| 2021/0154454 A1 | 5/2021 | Ignon et al. |
| 2021/0154455 A1 | 5/2021 | Ignon et al. |
| 2021/0177463 A1 | 6/2021 | Ignon et al. |
| 2021/0220631 A1 | 7/2021 | Ok et al. |
| 2021/0236342 A1 | 8/2021 | Long et al. |
| 2021/0236347 A1 | 8/2021 | Carver |
| 2021/0259914 A1 | 8/2021 | Holbert |
| 2021/0267625 A1 | 9/2021 | Carver |
| 2021/0268304 A1 | 9/2021 | Lee |
| 2021/0283421 A1 | 9/2021 | Kang et al. |
| 2021/0290430 A1 | 9/2021 | Kim |
| 2021/0330356 A1 | 10/2021 | Del Rosario et al. |
| 2021/0353922 A1 | 11/2021 | Ignon et al. |
| 2021/0361525 A1 | 11/2021 | Park et al. |
| 2021/0370089 A1 | 12/2021 | Anash |
| 2021/0393478 A1 | 12/2021 | Bhatti |
| 2021/0393974 A1 | 12/2021 | Kim et al. |
| 2021/0393975 A1 | 12/2021 | Eltorai et al. |
| 2021/0395071 A1 | 12/2021 | Zubrum et al. |
| 2021/0402208 A1 | 12/2021 | Edgar |
| 2022/0001198 A1 | 1/2022 | Lee |
| 2022/0071491 A1 | 3/2022 | Bae et al. |
| 2022/0072332 A1 | 3/2022 | Park et al. |
| 2022/0087891 A1 | 3/2022 | Goodman et al. |
| 2022/0111198 A1 | 4/2022 | Jung |
| 2022/0125706 A1 | 4/2022 | Horinek et al. |
| 2022/0126014 A1 | 4/2022 | Cederna et al. |
| 2022/0176092 A1 | 6/2022 | Quan et al. |
| 2022/0211988 A1 | 7/2022 | Ignon et al. |
| 2022/0226668 A1 | 7/2022 | Lee et al. |
| 2022/0241107 A1 | 8/2022 | Kim et al. |
| 2022/0241146 A1 | 8/2022 | Jeong |
| 2022/0401714 A1 | 12/2022 | Quan et al. |
| 2023/0012684 A1 | 1/2023 | Ignon et al. |
| 2023/0018295 A1 | 1/2023 | Ignon et al. |
| 2023/0033217 A1 | 2/2023 | Ignon et al. |
| 2023/0033761 A1 | 2/2023 | Ignon et al. |

FOREIGN PATENT DOCUMENTS

| | | |
|---|---|---|
| CA | 2 340 154 | 9/2002 |
| CN | 107920948 | 4/2018 |
| CN | 306995346 | 12/2021 |
| DE | 59 95 21 | 7/1934 |
| DE | 24 15 633 | 10/1975 |
| DE | 33 38 057 | 8/1984 |
| DE | 34 21 390 | 12/1985 |
| DE | 234 608 | 4/1986 |
| DE | 35 03 343 | 8/1986 |
| DE | 83 30 191 | 6/1987 |
| DE | 37 40 902 | 12/1988 |
| DE | 42 37 940 | 5/1993 |
| DE | 298 08 395 | 8/1998 |
| DE | 10 2004 015815 | 11/2005 |
| EP | 0 258 901 | 9/1987 |
| EP | 0 564 392 | 3/1993 |
| EP | 0 784 997 | 7/1997 |
| EP | 1238643 | 4/2000 |
| EP | 1 453 558 | 9/2004 |
| EP | 2206483 | 7/2010 |
| EP | 2544563 | 9/2015 |
| EP | 2 106 780 | 3/2016 |
| EP | 3 217 899 | 5/2016 |
| EP | 2865867 | 5/2016 |
| EP | 2240099 | 2/2018 |
| EP | 3 302 319 | 4/2018 |
| EP | 2967633 | 4/2018 |
| EP | 3319573 | 5/2018 |
| EP | 3 340 908 | 7/2018 |
| EP | 2451367 | 1/2020 |

(56) References Cited

FOREIGN PATENT DOCUMENTS

| | | |
|---|---|---|
| EP | 3388006 | 3/2020 |
| EP | 2618797 | 4/2020 |
| EP | 3237055 | 8/2020 |
| EP | 3795204 | 3/2021 |
| EP | 3437575 | 4/2021 |
| EP | 8794184-0001 | 12/2021 |
| ES | 1 037 776 | 4/1998 |
| FR | 2 712 172 | 5/1995 |
| FR | 2 773 461 | 7/1999 |
| GB | 1 372 609 | 10/1974 |
| GB | 2306351 | 5/1997 |
| IT | 553 076 | 12/1956 |
| IT | 118 49 22 | 3/1985 |
| JP | 53-118927 | 8/1963 |
| JP | H05-042060 | 2/1993 |
| JP | 1993-088552 | 12/1993 |
| JP | 1997-294747 | 11/1997 |
| JP | 2003-534881 | 11/2003 |
| JP | 2003-339713 | 12/2003 |
| JP | 2004-275721 | 10/2004 |
| JP | 2006-503627 | 2/2006 |
| JP | 2006-204767 | 10/2006 |
| JP | 2010/042243 | 2/2010 |
| JP | 2012527967 | 11/2012 |
| JP | 5508285 | 3/2014 |
| JP | 1581877 | 7/2017 |
| JP | 2018-527052 | 9/2018 |
| KR | 20-0280320 | 7/2002 |
| KR | 10-20070070173 | 7/2007 |
| KR | 10-2018-0030607 | 3/2018 |
| KR | 10-1836310 | 3/2018 |
| TW | 214226 | 9/2021 |
| WO | WO 1994/024980 | 11/1994 |
| WO | WO 1997/011650 | 3/1997 |
| WO | WO 2000/015300 | 3/2000 |
| WO | WO 00/79540 | 12/2000 |
| WO | WO 2001/93931 | 12/2001 |
| WO | WO 2003/073917 | 9/2003 |
| WO | WO 2004/037098 | 5/2004 |
| WO | WO 2005/061042 | 7/2005 |
| WO | WO 2005/070313 | 8/2005 |
| WO | WO 2006/018731 | 2/2006 |
| WO | WO 2006/031413 | 3/2006 |
| WO | WO 2007/114904 | 10/2007 |
| WO | WO 2008/012324 | 1/2008 |
| WO | WO 2009/088884 | 7/2009 |
| WO | WO 2009/097451 | 8/2009 |
| WO | WO 2010/068960 | 6/2010 |
| WO | WO 2011/006009 | 1/2011 |
| WO | WO 2011/110840 | 9/2011 |
| WO | WO 2012/145667 | 10/2012 |
| WO | WO 2013/030117 | 3/2013 |
| WO | WO 2014/091035 | 6/2014 |
| WO | WO 2014/151104 | 9/2014 |
| WO | WO 2016/052818 | 4/2016 |
| WO | WO 2016/106396 | 6/2016 |
| WO | WO 2017/007939 | 1/2017 |
| WO | WO 2017/111481 | 6/2017 |
| WO | WO 2021/018765 | 2/2021 |
| WO | WO 2021/113343 | 6/2021 |
| WO | WO 2022/099318 | 5/2022 |
| WO | WO 2023/039524 | 3/2023 |

OTHER PUBLICATIONS

Ditre et al., Effect of α-hydroxy acids on photoaged skin: A pilot clinical, histologic, and ultrastructural study, Journal of American Academy of Dermatology, Feb. 1996, vol. 34, No. 2, Part 1, pp. 187-195.

Harris et al., Combining Manual Dermasanding with Low Strength Trichloroacetic Acid to Improve Antinically Injured Skin, The Journal of Dermatologic Surgery and Oncology, Jul. 1994, vol. 20, No. 7, pp. 436-442.

HYDRAFACIAL® TOWER—User guide. Edge Systems. Revised Jun. 23, 2016. Page No. 16.

Microdermabrader Pepita Instruction Manual, Mattioli Engineering S.R.L., PEP_USA2.doc Rev 1.1, Sep. 29, 1997.

International Search Report for related PCT App. No. PCT/US2015/067531, dated Mar. 11, 2016.

Amazon, FAZJEUNE 7 Color LED Light, LED Face Mask Skin Rejevenation PDT Photon Facial Skin Care Mask Skin Tightening Lamp SPA Face Device Beauty Salon Equipment Anti-aging Remove Wrinkle, Customer reviewed on Sep. 2020, retrieved from internet at https://www.amazon.com/FAZJEUNE-Rejuvenation-Tightening-Equipment-Anti-aging/dp/B08B4M8RQQ/ref=psdc_11061121_t3_B08ZSPZSF4.

* cited by examiner

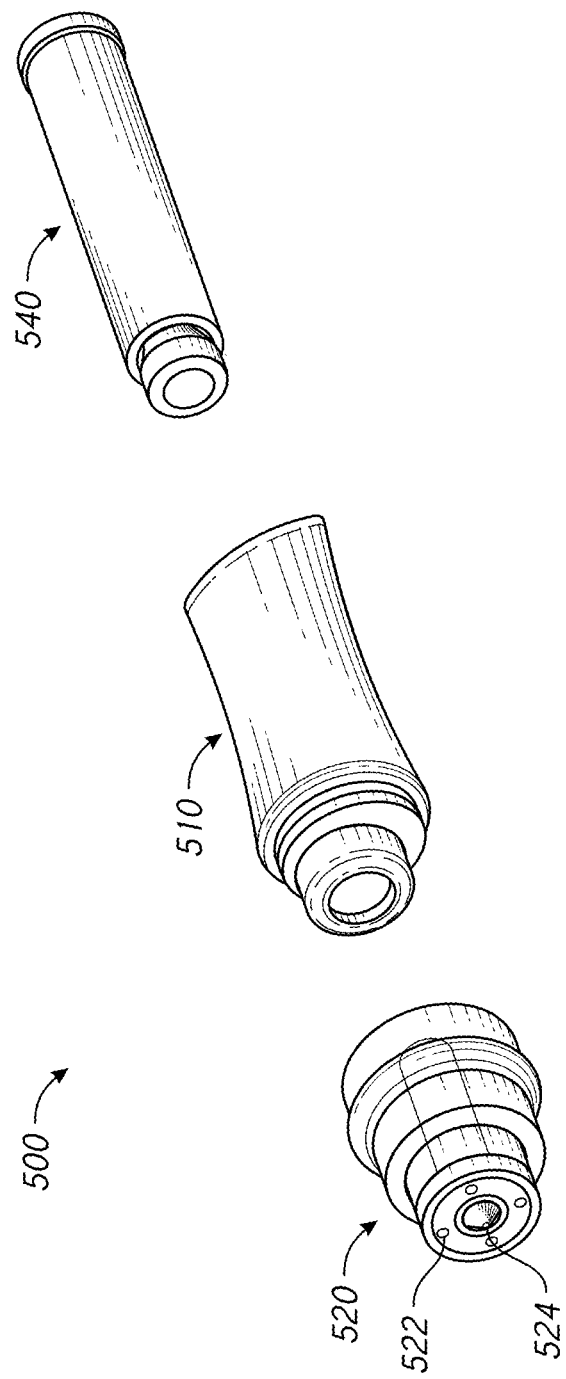

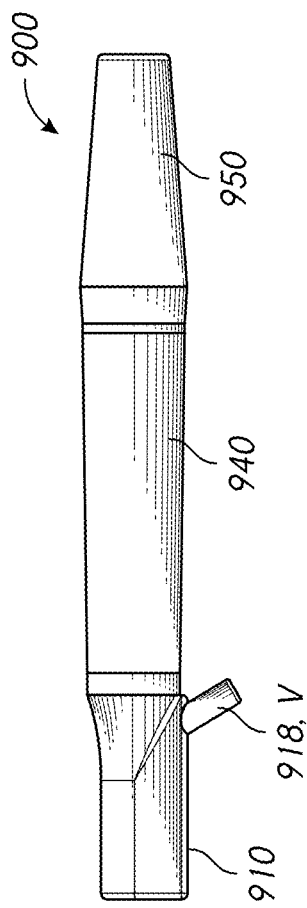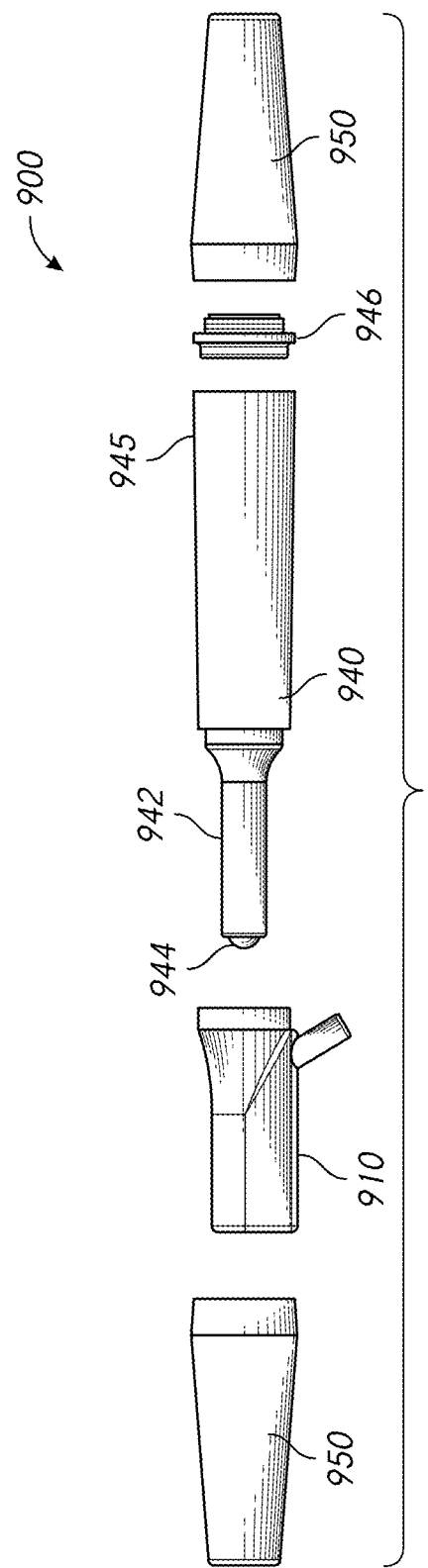
FIG. 9A
FIG. 9B

DEVICES AND METHODS FOR TREATING THE SKIN

RELATED APPLICATIONS

This application is a continuation of U.S. patent application Ser. No. 16/040,397 filed Jul. 19, 2018, which is a continuation of U.S. patent application Ser. No. 15/354,754 filed Nov. 17, 2016 and issued as U.S. Pat. No. 10,035,007 on Jul. 31, 2018, which is a continuation of U.S. patent application Ser. No. 14/998,375 filed Dec. 23, 2015 and issued as U.S. Pat. No. 9,498,610 on Nov. 22, 2016, which claims priority to U.S. Provisional Patent Application No. 62/096,493 filed Dec. 23, 2014, and U.S. Provisional Patent Application No. 62/235,479 filed Sep. 30, 2015. The entire contents of each of the priority applications listed above are incorporated herein by reference in their entireties.

BACKGROUND

Field

This application relates generally to skin treatment, and more specifically, to apparatuses, systems and methods for treating a person's skin using one or more rollerballs.

Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin. In some arrangements, skin can be treated by delivering one or more substances to the skin. In some instances, the application of suction along the skin surface can further enhance a skin treatment procedure.

SUMMARY

According to some embodiments, a skin treatment assembly comprises a handpiece comprising a distal end, the handpiece comprising a recess or cavity configured to receive a cartridge or other fluid container, a tip configured to be positioned along the distal end of the handpiece, the tip being configured to contact a skin surface of a subject during use, at least one rollerball configured to extend to or near the tip, wherein the at least one rollerball is configured to be in fluid communication with an interior of a cartridge or other fluid container secured to the handpiece, wherein the at least one rollerball is configured to contact the skin surface of the subject during use and to facilitate the delivery of fluids to said skin surface as the rollerball is moved relative to said skin surface, at least one suction conduit extending to the tip, wherein the at least one suction conduit is configured to be placed in fluid communication with a vacuum source to selectively apply suction to the tip during use, and at least one abrasive structure or member located on, near or along the tip, the at least one abrasive structure or member being configured to selectively exfoliate the subject skin during use.

According to some embodiments, the rollerball is secured to a distal end of the cartridge or other fluid container. In some embodiments, the rollerball is secured to the handpiece. In some embodiments, the rollerball is secured to the tip. In one embodiment, the rollerball is in direct fluid communication with the interior of the cartridge or other fluid container. In some embodiments, the rollerball is in indirect fluid communication with the interior of the cartridge or other fluid container. In some embodiments, the rollerball is in fluid communication with the interior of the cartridge or other fluid container via one or more fluid conduits or passages.

According to some embodiments, the area proximal to the at least one rollerball comprises one or more vanes that increase an effective surface area of an area immediately adjacent the at least one rollerball along or near the cartridge or other fluid container to help maintain fluids from the cartridge or other fluid container immediately adjacent the at least one rollerball. In some embodiments, the assembly further comprises a porous member immediately adjacent the at least one rollerball to ensure that fluid from the cartridge or other fluid container is placed in fluid communication with the at least one rollerball.

According to some embodiments, the tip comprises a peripheral lip, wherein the peripheral lip is sized, shaped and configured to contact a subject's skin tissue and generally form a seal along said skin tissue. In one embodiment, the at least one rollerball is positioned within an interior of the peripheral lip and extends to a height below the height of the peripheral lip. According to some embodiments, the cartridge or other fluid container is configured to be re-used during a subsequent treatment procedure.

According to some embodiments, a skin treatment assembly comprises a handpiece comprising a distal end, the handpiece being configured to receive a cartridge or being configured to be placed in fluid communication with a fluid source, a tip configured to be positioned along the distal end of the handpiece, the tip being configured to contact a skin surface of a subject during use, a rollerball configured to extend to or near the tip, wherein the rollerball is configured to be in fluid communication with an interior of a cartridge or other fluid container secured to the handpiece, wherein the rollerball is configured to contact the skin surface of the subject during use and to facilitate the delivery of fluids to said skin surface as the rollerball is moved relative to said skin surface, and at least one abrasive structure or member located on, near or along the tip, the at least one abrasive structure or member being configured to selectively exfoliate the subject skin during use.

According to some embodiments, the assembly further comprises at least one suction conduit extending to or near the tip, wherein the at least one suction conduit is configured to be placed in fluid communication with a suction source to selectively apply suction to the tip during use. In some embodiments, the rollerball is secured to a distal end of the cartridge or other fluid container. In one embodiment, the rollerball is secured to the handpiece. In some arrangements, the rollerball is secured to the tip.

According to some embodiments, the rollerball is in direct or indirect fluid communication with the interior of the cartridge or other fluid container. In some embodiments, the assembly further comprises a porous member adjacent (e.g., immediately adjacent) the at least one rollerball to ensure that fluid from the cartridge or other fluid container is placed in fluid communication with the at least one rollerball. In some embodiments, the tip comprises a peripheral lip, wherein the peripheral lip is sized, shaped and configured to contact a subject's skin tissue and generally form a seal along said skin tissue.

According to some embodiments, a skin treatment assembly comprises a handpiece comprising a distal end, the handpiece being configured to receive a fluid container, a tip positioned along the distal end of the handpiece, the tip being configured to contact a skin surface of a subject during use, at least one porous member configured to extend to or near the tip, wherein the at least one porous member is configured to be in fluid communication with an interior of a fluid container secured to the handpiece, wherein the at least one porous member is configured to contact the skin surface of the subject during use and to facilitate the delivery of fluids to said skin surface as the at least one porous member is moved relative to said skin surface, at least one suction conduit extending to the tip, wherein the at least one suction conduit is configured to be placed in fluid communication with a vacuum source to selectively apply suction to the tip during use, and at least one abrasive structure or member located on, near or along the tip, the at least one abrasive structure or member being configured to selectively exfoliate the subject skin during use.

According to some embodiments, the at least one porous member is secured to a distal end of the cartridge or other fluid container. In some embodiments, the at least one porous member comprises a wicking material. In some embodiments, the at least one porous member is secured to the handpiece. In some embodiments, the at least one porous member is secured to the tip. In one embodiment, the at least one porous member is in direct fluid communication with the interior of the cartridge or other fluid container.

According to some embodiments, the at least one porous member is in indirect fluid communication with the interior of the cartridge or other fluid container. In some embodiments, the at least one porous member is in fluid communication with the interior of the fluid container via one or more fluid conduits or passages. In one embodiment, the tip comprises a peripheral lip, wherein the peripheral lip is sized, shaped and configured to contact a subject's skin tissue and generally form a seal along said skin tissue. In some embodiments, the cartridge or other fluid container is configured to be re-used during a subsequent treatment procedure.

According to some embodiments, a skin treatment assembly comprises a handpiece comprising a distal end, the handpiece being configured to receive a fluid container, a tip positioned along the distal end of the handpiece, the tip being configured to contact a skin surface of a subject during use, a porous member configured to extend to or near the tip, wherein the porous member is configured to be in fluid communication with an interior of a fluid container secured to the handpiece, wherein the porous member is configured to contact the skin surface of the subject during use and to facilitate the delivery of fluids to said skin surface as the porous member is moved relative to said skin surface, and at least one suction conduit extending to the tip, wherein the at least one suction conduit is configured to be placed in fluid communication with a vacuum source to selectively apply suction to the tip during use.

According to some embodiments, the at least one porous member is secured to a distal end of the cartridge or other fluid container. In some embodiments, the at least one porous member comprises a wicking material. In one embodiment, the at least one porous member is secured to the handpiece. In some embodiments, the at least one porous member is secured to the tip. In some embodiments, the at least one porous member is in direct fluid communication with the interior of the cartridge or other fluid container. In some embodiments, the at least one porous member is in indirect fluid communication with the interior of the cartridge or other fluid container. In some embodiments, the at least one porous member is in fluid communication with the interior of the fluid container via one or more fluid conduits or passages.

According to some embodiments, the assembly further comprises at least one abrasive structure or member located on, near or along the tip, the at least one abrasive structure or member being configured to selectively exfoliate the subject skin during use. In some embodiments, the at least one abrasive structure or member comprises a ridge or portion comprising a sharp surface.

According to some embodiments, a method of treating a skin surface of a subject comprises conducting a first skin treatment procedure on a subject at a professional facility, wherein the first skin treatment procedure comprises skin treatment using a handpiece, the handpiece comprising a tip and a removable cartridge, the tip being configured to contact a skin surface of a subject during use, wherein a rollerball is configured to extend to or near the tip, wherein the rollerball is configured to be in fluid communication with an interior of a cartridge or other fluid container secured to the handpiece, wherein the a rollerball is configured to contact the skin surface of the subject during use and to facilitate the delivery of fluids to said skin surface as the rollerball is moved relative to said skin surface, at least partially exfoliating a skin surface of a subject at the professional facility by moving the tip relative to the subject's skin surface, providing the cartridge or other fluid container to the subject following the first skin treatment procedure, and instructing the subject to conduct a second skin treatment procedure following the first skin treatment procedure, wherein the second skin treatment procedure is performed by the subject, the second skin treatment procedure comprising providing delivering a volume of fluids from the cartridge or other fluid container to a skin surface of the subject.

According to some embodiments, the method further comprises a third skin treatment procedure following the second skin treatment procedure, wherein the third skin treatment procedure is performed at a professional facility. In some embodiments, the subject brings the cartridge or other fluid container to the professional facility. In some arrangements, the second skin treatment procedure does not comprise exfoliation. In one embodiment, the second skin treatment procedure comprises only fluid delivery to the skin surface of the subject.

According to some embodiments, the first skin treatment procedure comprises skin exfoliation, wherein the tip comprises at least one abrasive surface configured to at least partially exfoliate skin when the handpiece is moved relative to the subject's skin. In some arrangements, the at least one abrasive surface comprises at least one sharp surface along the tip. In one embodiment, the at least one sharp surface comprises a spiral member extending distally from a base surface of the tip. In some arrangements, the at least one sharp surface comprises a post member extending distally from a base surface of the tip. In some embodiments, the cartridge or other fluid container comprises a cap to protect the rollerball following the first and second skin treatment procedures.

According to some embodiments, a method of treating a skin surface of a subject includes conducting a first skin treatment procedure on a subject at a treatment facility, wherein the first skin treatment procedure comprises skin treatment using a handpiece, the handpiece comprising a tip and a cartridge configured to be positioned along the distal end of the handpiece, the tip being configured to contact a skin surface of a subject during use, wherein at least one of a rollerball and a porous member is configured to extend to or near the tip, wherein the at least one of a rollerball and a porous member is configured to be in fluid communication with an interior of a cartridge or other fluid container secured to the handpiece, wherein the at least one of a rollerball and a porous member is configured to contact the skin surface of the subject during use and to facilitate the delivery of fluids to said skin surface as the rollerball or porous member is moved relative to said skin surface, at least partially exfoliating a skin surface of a subject at the treatment facility by moving the tip relative to the subject's skin surface;

providing the cartridge or other fluid container to the subject following the first skin treatment procedure, and instructing the subject to conduct a second skin treatment procedure following the first skin treatment procedure, wherein the second skin treatment procedure is performed by the subject, the second skin treatment procedure comprising providing delivering a volume of fluids from the cartridge or other fluid container to a skin surface of the subject.

According to some embodiments, the method further comprises a third skin treatment procedure following the second skin treatment procedure, wherein the third skin treatment procedure is performed at a treatment facility. In some embodiments, the subject brings the cartridge or other fluid container to the treatment facility. In some embodiments, the second skin treatment procedure does not comprise exfoliation. In one embodiment, the second skin treatment procedure comprises only fluid delivery to the skin surface of the subject.

According to some embodiments, the first skin treatment procedure comprises skin exfoliation, wherein the tip comprises at least one abrasive surface configured to at least partially exfoliate skin when the handpiece is moved relative to the subject's skin. In some embodiments, the at least one abrasive surface comprises at least one sharp surface along the tip. In some embodiments, the at least one sharp surface comprises a spiral member extending distally from a base surface of the tip. In one embodiment, the at least one sharp surface comprises a post member extending distally from a base surface of the tip. In some arrangements, the cartridge or other fluid container comprises a cap to protect the at least one of a rollerball and a porous member following the first and second skin treatment procedures.

According to some embodiments, a skin treatment assembly comprises a handpiece comprising a distal end, the handpiece comprising a recess or cavity configured to receive a cartridge or other fluid container, a tip configured to be positioned along the distal end of the handpiece, the tip being configured to contact a skin surface of a subject during use, and at least one rollerball configured to extend to or near the tip, wherein the rollerball is configured to be in fluid communication with an interior of a cartridge or other fluid container secured to the handpiece, wherein the at least one rollerball is configured to contact the skin surface of the subject during use and to facilitate the delivery of fluids to said skin surface as the rollerball is moved relative to said skin surface.

According to some embodiments, the rollerball is secured to a distal end of the cartridge or other fluid container. In one embodiment, the rollerball is secured to the handpiece. In some embodiments, the rollerball is secured to the tip.

According to some embodiments, the rollerball is in direct fluid communication with the interior of the cartridge or other fluid container. In some embodiments, the rollerball is in indirect fluid communication with the interior of the cartridge or other fluid container. In one embodiment, the rollerball is in fluid communication with the interior of the cartridge or other fluid container via one or more fluid conduits or passages.

According to some embodiments, the assembly further comprising at least one suction conduit extending to the tip, wherein the at least one suction conduit is configured to be placed in fluid communication with a vacuum source to selectively apply suction to the tip during use. In one embodiment, the tip comprises a peripheral lip, wherein the peripheral lip is sized, shaped and configured to contact a subject's skin tissue and generally form a seal along said skin tissue.

According to some embodiments, the assembly further comprises at least one abrasive structure or member located on, near or along the tip, the at least one abrasive structure or member being configured to selectively exfoliate the subject skin during use. In some embodiments, the cartridge or other fluid container is configured to be re-used during a subsequent treatment procedure.

BRIEF DESCRIPTION OF THE DRAWINGS

These and other features, aspects and advantages of the present application are described with reference to drawings of certain embodiments, which are intended to illustrate, but not to limit, the present inventions. It is to be understood that these drawings are for the purpose of illustrating the various concepts disclosed herein and may not be to scale.

FIG. 5 illustrates an exploded perspective view an assembly comprising a rollerball for use with a skin treatment system according to one embodiment;

FIGS. 9A and 9B illustrate different views of an assembly comprising a rollerball for use with a skin treatment system according to one embodiment;

DETAILED DESCRIPTION

Although the various embodiments of a handpiece assembly have specific relevance to a skin treatment system, the features, advantages and other characteristics disclosed herein may have direct or indirect applicability in other applications, such as, for example, medical devices, mechanical devices and/or the like. For instance, the various configurations disclosed herein have specific relevance to exfoliation and/or other removal of the superficial layer of skin cells. However, the various systems, devices and methods disclosed herein can be modified and/or otherwise configured for use with skin treatment procedures that target removal of deeper tissue layers, as desired or required.

Figure 1:
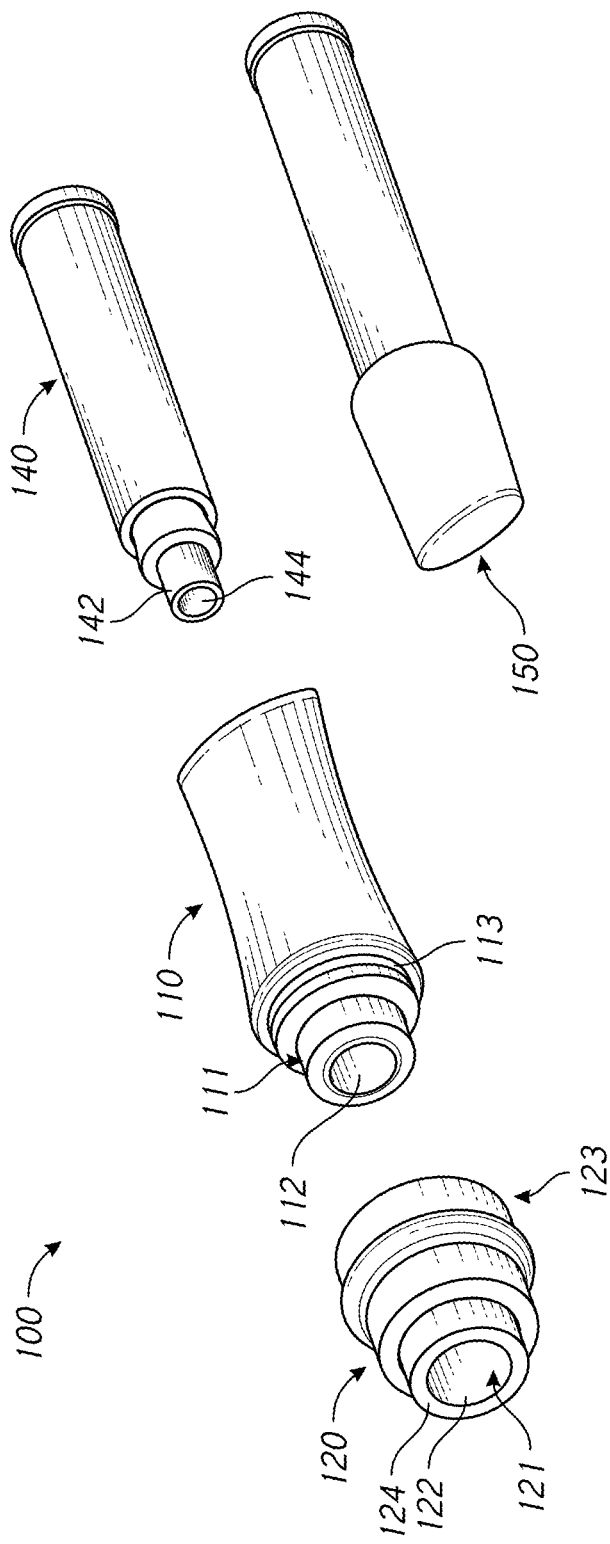
FIG. 1 illustrates an exploded perspective view an assembly comprising a rollerball for use with a skin treatment system according to one embodiment.

FIG. 1 illustrates one embodiment of an assembly 100 configured for use with a skin treatment system. As shown, the assembly 100 can include one or more components or portions that are configured to secure to one another. In some embodiments, for example, the assembly 100 comprises a handpiece 110 that is adapted to receive a tip 120 along its distal end. The tip 120 can be revocable from the handpiece 110, as depicted in FIG. 1. However, in other embodiments, the tip 120 can be permanently attached to the handpiece 110 and/or can otherwise be integrated with the handpiece 110, as desired or required. In some embodiments, the tip 120 can be removable and disposable. The use of such removable tips 120 can facilitate the use of the assembly (e.g., between different subjects) and/or can permit a user to customize a skin treatment procedure. For example, in some embodiments, the tip 120 comprises one or more abrasive features, components and/or portions to help abrade or exfoliate skin as the handpiece is moved relative to skin. For example, in some arrangements, the tip 120 comprises one or more of the following: one or more spiral members, cylinders, posts, gritty surfaces, other abrasive members or features, ridges, sharp edges, diamonds and/or the like. Additional details regarding the tips are included in U.S. patent application Ser. No. 11/392,348, filed on Mar. 29, 2006 and issued as U.S. Pat. No. 8,048,089 on Nov. 1, 2011, the entirety of which is incorporated by reference herein.

In other embodiments, however, the tip need not include any abrasive and/or other components or features that are configured to abrade skin. Thus, in some configurations, the tip 120 can simply provide a mechanism or means by which fluids and/or other components are selectively delivered to the skin surface.

With continued reference to FIG. 1, the handpiece 110 is configured to removably receive a cartridge 140 or other container. For example, the cartridge 140 can be inserted within a corresponding recess of the handpiece 110 (e.g., along the proximal end of the handpiece 110). In other arrangements, however, the cartridge 140 or other container can be positioned along any other portion of the handpiece 110. In other embodiments, the cartridge 140 can be placed in fluid communication or otherwise fluidly coupled to the handpiece 110 and/or the tip 120.

For any of the assembly embodiments disclosed herein, depending on the specific treatment protocol being administered to a subject, a cartridge can comprise one or more of the following: skin tightening agents, platelet-rich plasma (PRP), exfoliation agents, peptides, bleaching agents, anti-acne agents, human growth factors, cytokines, soluble collagen, antioxidants, matrix proteins, Epicatechin, Catechin and/or other phenols and/or other anti-oxidants, neurotoxins, serums, salicylic acid, other anti-acne acids and materials, microcapsules, capsules, other time-release products and substances, water (e.g., distilled, tap water, filtered, etc.), saline, other dilution agents, dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance from one or more internal/external fluid sources.

Any of the assembly embodiments disclosed herein comprise at least one rollerball, a wicking, porous and/or other absorptive member and/or other member to facilitate the delivery of one or more fluids and/or other substances from a fluid source (e.g., cartridge, other container, etc.) to the skin surface being treated (e.g., via a distal tip of the assembly). A portion or area of the rollerball or other member can be fluid communication (e.g., directly or indirectly) with the cartridge or other fluid source. In some embodiments, as the assembly is moved relative to a subject's skin surface, the rollerball and/or other member (e.g., wicking member, other porous or absorptive member, etc.) contacts the skin surface and rolls along the skin surface. In so doing, the rollerball can advantageously deliver fluid from the fluid source (e.g., cartridge, a manifold, etc.) to the tip and working surface along the assembly-skin interface. Accordingly, the rollerball and/or other delivery member can facilitate the delivery of fluids to the skin surface during a treatment procedure as the assembly is moved relative to such a surface.

In any of the embodiments disclosed herein, the rollerball can be secured within a housing or other retention assembly (e.g., of the cartridge, handpiece, tip, etc.), allowing it to rotate. The rollerball and/or other member (e.g., absorptive, wicking and/or other member) can be removably (e.g., replaceably) or permanently maintained within a retention assembly or other portion of the assembly, as desired or required. For example, the rollerball can be removed and replaced (e.g., to change its materials or other properties, to change it smoothness, texture or porosity, to change its size, to replace a damaged or used rollerball, etc.). However, in other configurations, the rollerball or other member is configured to not be removed from the corresponding housing or retention assembly.

In FIG. 1, the handpiece 110 of the assembly 100 comprises a central opening 112 along its distal end 111. The opening 112 can be sized, shaped and otherwise configured to at least partially receive the rollerball 144 located along the distal end 142 of the cartridge 140. Thus, in some embodiments, the cartridge is configured to releasably engage the handpiece. The cartridge 140 and handpiece can be releasably secured to one another using one or more attachment features, devices and/or methods, such as, for example, a threaded connection, a friction fit or pressure fit connection, a flanged connection, a rotatable connection (e.g., comprising a recess and a corresponding tab), other mechanical or non-mechanical connections and/or the like. Regardless of the exact attachment or securement mechanism between the handpiece and the cartridge, once the cartridge has been adequately positioned relative to the handpiece, the rollerball 144 can be configured to extend at least partially along the distal end of the handpiece 110. In some arrangements, the cartridge or other container 140 comprises a dummy cartridge that is configured to be placed in fluid communication with a fluid delivery system (e.g., a manifold-based system). Thus, in such configurations, fluid from one or more fluid sources can be selectively delivered to the cartridge 140 and to the distal end (e.g., tip 120) using one or more fluid conduits, as desired or required.

With continued reference to FIG. 1, the distal tip 120 can be configured to be removably secured to the handpiece 110 (e.g., along the distal end 111 of the handpiece 110 and the proximal end 123 of the tip 120. As with any other connections between adjacent components or portions of the assembly 100, one or more O-rings 113 or other sealing members can be positioned along the interface of the tip 120 and the handpiece 110 (e.g., to prevent or reduce the likelihood of leaks), in accordance with a desired or required arrangement.

As depicted in FIG. 1, the tip 120 can include a central opening 122 along its distal end that coincides with (e.g., shares the same longitudinal axis as) the rollerball 144 and the opening 112 of the handpiece 110. Thus, when the assembly 100 is properly assembled or otherwise put together, the rollerball 144 can be adjacent the area defined by the central opening 122 of the tip 120. In some embodiments, the tip comprises a peripheral lip 124 that circumscribes a central area (e.g., an area at least partially defined by the central opening 122 of the tip 120). Further, the rollerball 144 can be sized, shaped and otherwise configured to be positioned within the central area circumscribed by the lip 124 of the tip 120. In some arrangements, the distal end of the rollerball 144 is recessed relative to the distal end of the tip's lip 124. However, in other configurations, the distal end of the rollerball 144 can be aligned with or generally aligned with the distal end of the lip 124 of the tip 120, as desired or required.

According to some embodiments, as discussed in greater detail herein, the assembly 100 is configured to be selectively coupled to a vacuum or suction source. Thus, the tip, handpiece, cartridge or other fluid source and/or any other portion of the assembly 100 can include one or more fluid passages, openings, ports, valves and/or any other features to enable the vacuum or suction capabilities of the assembly 100. For example, the tip can include one or more suction ports that are aligned with one or more fluid conduits (e.g., internal and/or external passages) of the handpiece 110. As discussed in greater detail herein, any of the disclosed embodiments can include one or more features (e.g., peripheral lip, interior feature such as posts or cylindrical members, spiral members, abrasive pad or members, and/or the like) that are configured to selectively abrade tissue. For example, in any of the embodiments, the peripheral lip 124 can be configured to at least partially abrade and/or otherwise remove skin tissue when the handpiece assembly is moved relative to the skin surface.

Regardless of the exact fluid components that an assembly 100 comprises to enable it to selectively deliver a vacuum or suction force to the tip 120, the selective activation of such suction or vacuum can facilitate a skin treatment procedure and/or the use of the assembly. For example, in some embodiments, the use of suction can help with the delivery of fluids from a fluid source to the tip. In some embodiments, the use of vacuum can help create a seal between a periphery (e.g., lip) of the tip and the skin tissue, which in turn, can help with the delivery of fluids to the skin interface. As noted above, the use of a lip and/or any other interior members can assist with the at least partial abrading of tissue when the handpiece assembly is moved relative to a skin surface (e.g., especially when vacuum is being applied to the tip).

As illustrated in FIG. 1, in some embodiments, the cartridge, container or other fluid source 140 can be configured to be re-used over a period of time. For example, the distal end 142 of the cartridge 140 can be protected between uses by a cap or other sealing member 150. Thus, the rollerball 144 of the cartridge 140 can be protected when not in use. The cartridge 140 can be re-used between various treatment procedures by a professional. In some embodiments, the cartridge 140 can be provided to the subject for application of fluid at home between visits to a professional.

In any of the embodiments disclosed herein or variations thereof, the tip and/or the entire handpiece assembly (e.g., especially in arrangements where the tip is not removable from the rest of the handpiece assembly) can be disposable. Thus, the tip can be configured for a single use prior to disposal. Accordingly, the tip can include one or more thermoplastic and/or other materials that are well suited for a single use application. Alternatively, the tip and/or other components of the assembly can include one or more metals, alloys, other rigid and/or semi-rigid materials and/or other materials that enable a user to re-use such items, as desired or required. For example, metallic and/or alloy-based tips (e.g., comprising stainless steel, titanium, platinum, etc.) can be configured to be autoclaved and/or otherwise sterilized between uses.

FIG. 1 illustrates the device being capped along its distal end using a cap or other enclosure 150. As shown, such a cap or other enclosure 150 can help isolate the rollerball and/or other distal member (e.g., wicking member, absorptive member, etc.) from the surrounding environment. This can be helpful when the handpiece assembly 100 is not in use to ensure that contaminants and/or other substances do not taint the rollerball, another member that facilitates delivery of fluids and/or other materials to the tip and/or other portion of the distal end of the assembly 100 that may contact a targeted skin surface.

Figure 2:
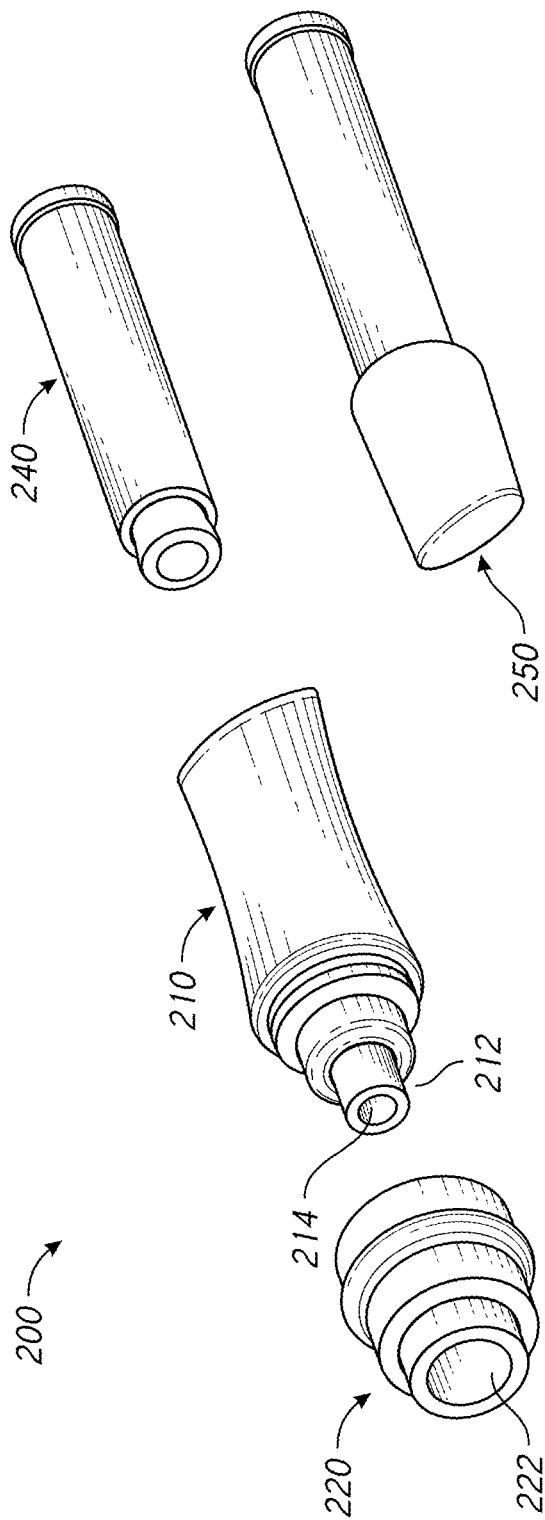
FIG. 2 illustrates an exploded perspective view an assembly comprising a rollerball for use with a skin treatment system according to one embodiment.

FIG. 2 illustrates a different embodiment of an assembly 200 configured for skin treatment. The assembly 200 is similar to the one depicted in FIG. 1 and described above; however, the rollerball 214 in the assembly 200 of FIG. 2 is positioned along the distal end 212 of the handpiece 210, instead of the cartridge 240. As with other embodiments disclosed and illustrated herein, the handpiece can be configured to receive a tip 220 along the distal end 212 of the handpiece 210. The distal end 212 of the handpiece 210 with the rollerball 214 can be configured to pass through the interior of the tip 220 and extend toward a central opening 222 of the tip. Thus, as the assembly 200 is moved relative to a skin surface, the rollerball 214 can at least partially engage the skin surface, and with movement along such skin surface, can help deliver fluids from a cartridge or other fluid source 240 to the subject's skin. As discussed above with reference to the embodiment illustrated in FIG. 1, the delivery of fluids to the skin surface can be facilitated, in certain configurations, with the application of suction or vacuum. In addition, the cartridge, container or other fluid source 240 can include a cap or other enclosure member 250 that is configured to be secured to the distal end of the cartridge 240. Although in the depicted arrangement the cartridge 240 does not include a rollerball along its distal end, the cap 250 can ensure that the contents of the cartridge and/or other portions of the cartridge 240 that may be exposed to contamination are kept clean and are otherwise protected between uses.

Further, as noted above, the tip 220 can include one or more abrasive features, surfaces and/or the like such that when the tip is moved relative to a targeted skin surface (e.g., especially upon activation of a vacuum source that draws the tip toward and/or engaged with the targeted skin surface), at least portions of the targeted skin surface can be selectively abraded or otherwise removed. For example, in some arrangements, the peripheral lip of the tip 220 can be configured to at least partially abrade or otherwise remove skin tissue when the assembly 200 is moved relative to a subject's skin surface. Such abrasive features or designs can be incorporated into any embodiments disclosed herein or variations thereof.

Figure 3:
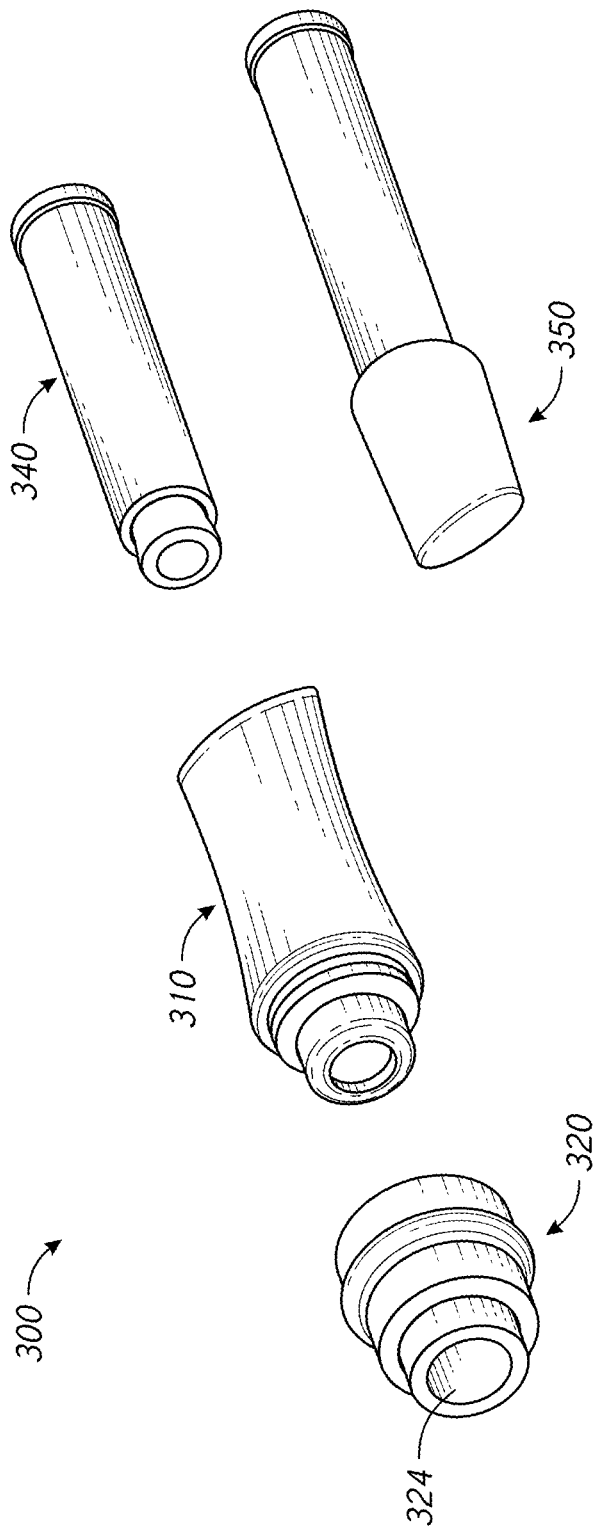
FIG. 3 illustrates an exploded perspective view an assembly comprising a rollerball for use with a skin treatment system according to one embodiment.

FIG. 3 illustrates an exploded perspective view of yet another embodiment of an assembly 300 that can be used to perform a skin treatment procedure. As shown, and similar to other configurations depicted herein, the assembly 300 can comprise a cartridge 340, a handpiece 310 that is sized, shaped and otherwise configured to receive a cartridge and a distal tip 320. The various components of the assembly 300 can be configured to removably secure to each other. However, in other embodiments, the two or more of the components can be permanently or semi-permanently secured to each other (e.g., so as to form a monolithic or unitary structure). Such a configuration, wherein two or more portions form a unitary or monolithic structure, can be incorporated into any of the embodiments disclosed herein or variations thereof.

With continued reference to FIG. 3, unlike the configurations depicted in FIGS. 1 and 2, the rollerball and/or other member (e.g., absorptive member, wicking member, porous member, etc.) 324 is positioned along the tip 320. Thus, in some embodiments, the rollerball 324 is configured to be in fluid communication, directly or indirectly, with an internal reservoir or other fluid-containing portion of the cartridge, container or other fluid source 340. For example, in some arrangements, the rollerball 324 of the tip 320 is configured to receive fluid from the cartridge 320 via one or more passages, channels or other intermediate fluid reservoirs or members that extend at least partially from the cartridge 340 to the tip 320. As with other embodiments disclosed herein, the cartridge 340 can be re-used in different treatment procedures. For example, the subject can be provided with any unused cartridges 340 following a visit to a professional. Thus, depending on the particular skin treatment protocol being used, the subject can simply bring one or more unused cartridges 340 to the next scheduled treatment procedure and/or can be apply certain fluids to his or her skin between visits, as desired or required by a particular treatment protocol.

Figure 4:
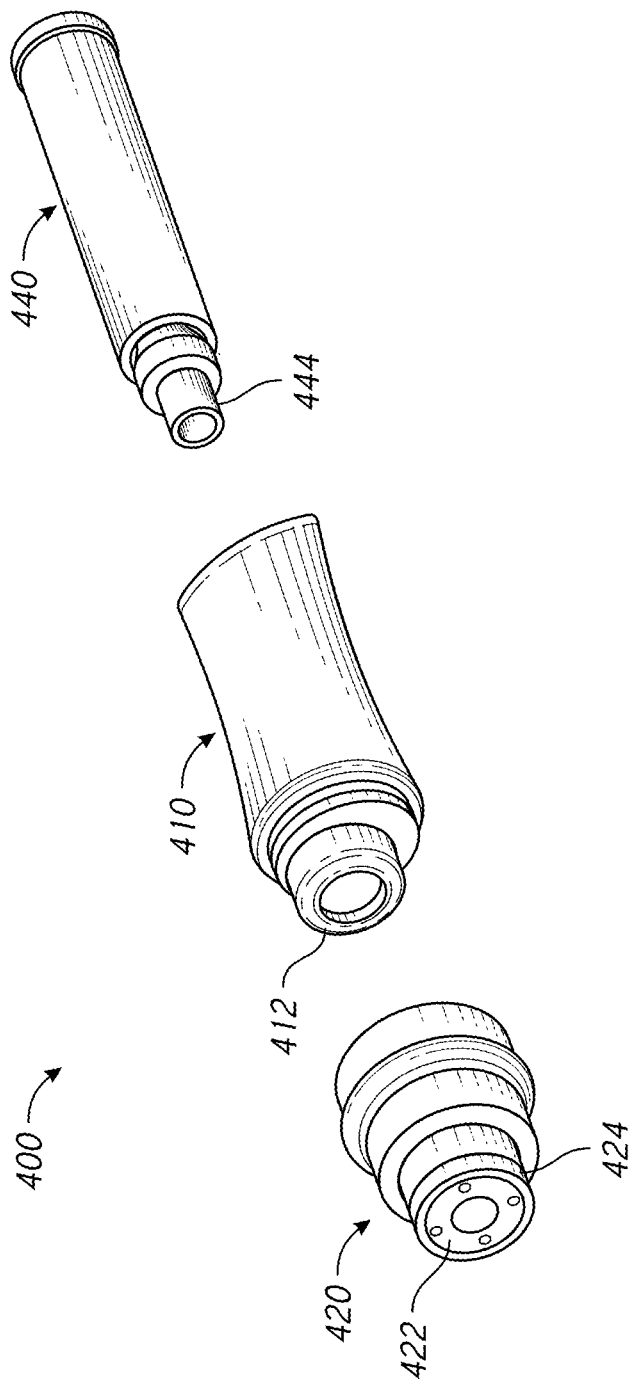
FIG. 4 illustrates an exploded perspective view an assembly comprising a rollerball for use with a skin treatment system according to one embodiment.

FIG. 4 illustrates an exploded perspective view of an assembly 400 that is a variation of the arrangement depicted in FIG. 1. As in FIG. 1, the depicted assembly 400 comprises a cartridge 440 having a rollerball 444 along its distal end. The cartridge, container or other fluid source 440 is sized, shaped and otherwise configured to be inserted and secured, at least partially, within a corresponding recess or opening along the proximal end of a handpiece 410. As with the embodiment of FIG. 1, the rollerball 444 along the distal end of the cartridge, container or other fluid source 440 can extend to, near and/or past the distal opening 412 of the handpiece 410. Accordingly, as the assembly 400 is moved relative to a skin surface of a subject, the rollerball 444 can at least partially contact the skin surface and rotate, thereby drawing out fluid, either directly or indirectly, from the cartridge or other fluid source 440. In some embodiments, as discussed herein, contact between the rollerball 444 and the skin surface and/or the drawing of liquid toward the skin surface is facilitated by the activation of a vacuum or suction force along the tip 420. For example, a peripheral lip 424 of the tip 420 can extend outwardly so as to contact skin tissue and circumscribe an interior region of the tip during use. The lip 424 can, therefore, be used to create a complete or partial seal with the skin surface being treated during use. Accordingly, in such configurations, once a vacuum or suction force is activated, skin located within an interior of the peripheral lip 424 of the tip 420 can be at least partially drawn into toward the assembly to facilitate and/or enhance contact between the rollerball 444 and the skin surface. Also, as noted herein, such embodiments that utilize suction can help deliver or enhance the delivery of fluids from the cartridge or other fluid source 440 to the tip. Further, as discussed in greater detail herein, the peripheral lip 424 and/or any other member (e.g., one or more interior members or portion of the tip, such as, posts, other cylindrical members, spiral members, abrasive pads and/or the like) can be used to at least partially abrade skin tissue as the tip is moved relative to a targeted skin surface.

As illustrated in FIG. 4 and discussed in greater detail herein, the tip can include one or more abrasive members or features 422. For example, such abrasive members or features 422 can comprise one or more sharp edges or surfaces, spiral members, posts, grit or other roughened members or surfaces and/or the like. As noted above, for any of the embodiments disclosed herein or variations thereof, the peripheral lip can be shaped and otherwise configured to abrade tissue. Additional details regarding the various abrasive members or features that can be incorporated into the tip to help exfoliate a subject skin are provided in U.S. patent application Ser. No. 11/392,348, filed on Mar. 29, 2006 and issued as U.S. Pat. No. 8,048,089 on Nov. 1, 2011, the entirety of which is incorporated by reference herein.

Further, in any of the embodiments disclosed herein or variations thereof, one or more materials can be positioned on, which, along and/or near the tip. In some arrangements, such materials are positioned along a cavity or similar retention member (e.g., an interior of a post or other interior member, another cavity or member along or near the tip, etc.), as desired or required. Such materials can be configured to at least partially dissolve or otherwise be released in the presence of water, other liquid or fluid and/or another diluting agent. In some embodiments, such materials are stored in porous or absorptive members and are configured to at least partially release from such members in the presence of a liquid. Accordingly, in such configurations, the various serums and/or other treatment materials that are desired to be delivered to a subject's skin surface for a particular treatment protocol can be embedded or otherwise located along or near the tip. Water, saline and/or another diluting agent can be advantageously delivered to the tip to selectively dilute and release the serums and/or other treatment materials to the subject skin. Additional details regarding positioning dissolvable or otherwise releasable materials on or near the tip of an assembly are provided in U.S. patent application Ser. No. 11/392,348, filed on Mar. 29, 2006, and issued as U.S. Pat. No. 8,048,089 on Nov. 1, 2011, and U.S. patent application Ser. No. 12/832,663, filed on Jul. 8, 2010 and issued as U.S. Pat. No. 8,814,836 on Aug. 26, 2014, the entireties of both of which are hereby incorporated by reference herein.

Another variation of an assembly 500 that comprises a rollerball 524 to facilitate the delivery of fluids to a skin surface is illustrated in FIG. 5. As shown, the assembly 500 comprises a cartridge or other fluid source 540 that is configured to be positioned within a corresponding recess or area along the proximal end of a handpiece 510. In addition, as discussed herein with reference to other embodiments, a removable tip 520 can be configured to be secured to the distal end of the handpiece 510. In the depicted embodiment, the tip 520 comprises both a rollerball 524 and an abrasive surface or structure 522. Thus, in such a configuration, moving the assembly 500 relative to a skin surface of a subject can assist with the delivery of fluids to the skin surface, while causing skin tissue to be abraded or exfoliated.

Figure 6A:
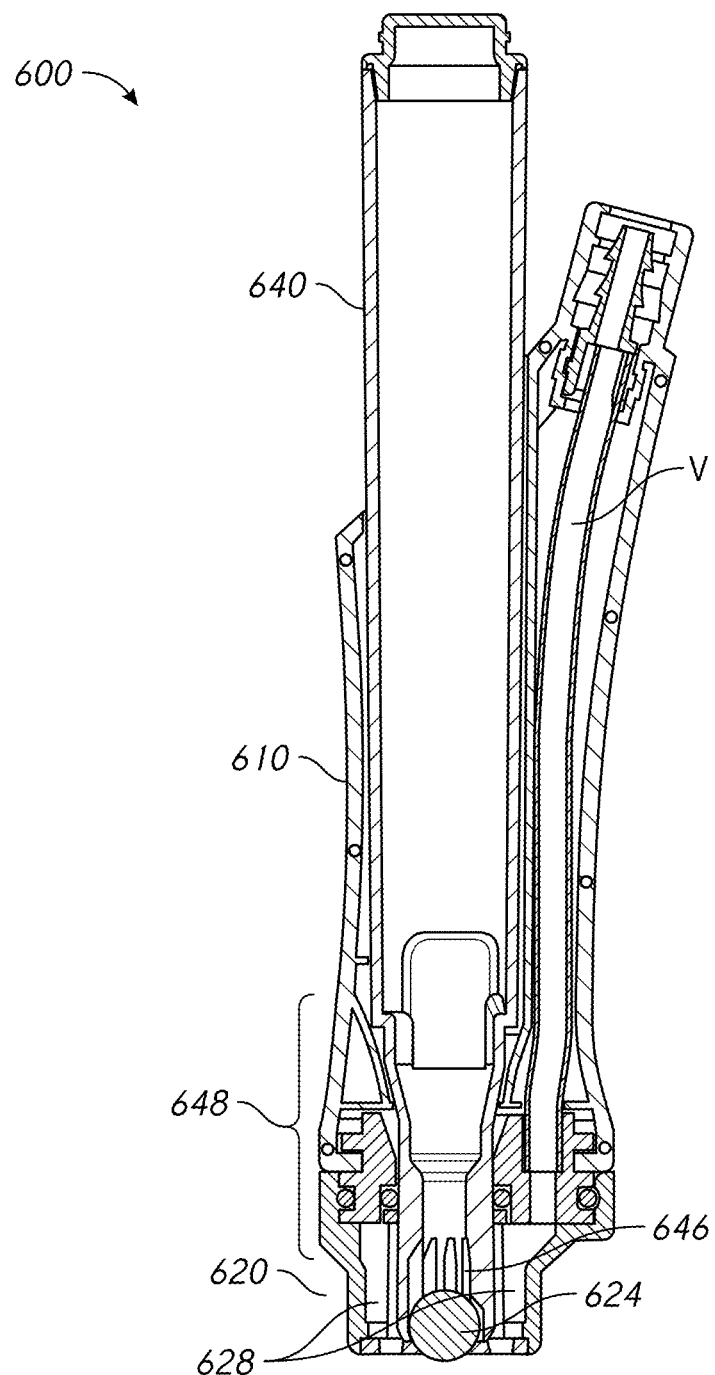
FIG. 6A illustrates a cross-sectional view of an assembly comprising a rollerball for use with a skin treatment system according to one embodiment.

A side cross-sectional side view of another embodiment of a skin treatment assembly 600 comprising a rollerball 624 is illustrated in FIG. 6A. As shown, the cartridge or other fluid source 640 can be sized, shaped and otherwise configured to be positioned within a recess or other opening of the handpiece 610. In the illustrated embodiment, the rollerball 624 is positioned along a distal end of the cartridge 640. However, in other configurations, as discussed herein with reference to FIGS. 2, 3 and 5, the rollerball can be positioned on the handpiece or the tip, as desired or required.

With continued reference to FIG. 6A, the cartridge 640 can include a tapered portion 648 along its distal end. Such a tapered portion can include two or more vanes, baffles and/or other separation members 646 that increase the surface area of the fluid channel or conduit of the cartridge 640 along the end of the cartridge near the rollerball 624. The vanes or baffles 646 can help maintain liquid contained within the cartridge 640 near the distal end of the cartridge 640. For example, such features can help retain liquids therein as a result of the surface tension of the liquid. Accordingly, in some embodiments, at least a volume of liquid can be maintained at or near the distal end of the cartridge 640, and thus the rollerball 624. In some arrangements, therefore, a minimum volume of liquid and/or other material contained within the cartridge 640 can be positioned adjacent the rollerball 624 to permit such liquid and/or other material to be selectively delivered to the skin when the assembly 600 is moved relative to the subject's skin surface. In some embodiments, for example, at least some volume of liquid can be disposed at or near the distal end of the cartridge regardless of the exact orientation of the assembly (e.g., when gravity tends to move the liquid away from the distal end of the cartridge).

As illustrated in FIG. 6A, the cartridge 640 can be sized, shaped and configured to extend past the distal end of the handpiece 610. In some embodiments, the distal end of the cartridge 640 can extend partially or completely within and/or through a tip 620 that is secured to the distal end of the handpiece 610. In the illustrated embodiment, the rollerball 624 extends past the distal end of the tip 624. However, in other arrangements, the rollerball 624 is flush (or generally flush) with or recessed relative to the distal end of the tip 624.

Further, as shown in FIG. 6A, the tip 624 can comprise one or more vacuum or suction ports and passages 628 that place the distal end of the tip 624, and thus, the assembly 600, in fluid communication with a vacuum source (not shown). The tip 624 can include one, two or more suction ports and/or passages 628, as desired or required. The quantity, size, shape, orientation and/or other details about any suction ports/passages 628 included on a tip can vary, depending on the particular design. As depicted in the cross-sectional view of FIG. 6A, the suction ports and passages 628 can be configured to be fluid communication with one or more vacuum or suction conduits or passages V of the handpiece 610. The vacuum or suction conduit(s) V can be positioned within an interior portion of the handpiece 610, as illustrated in FIG. 6A. However, in other embodiments, the vacuum or suction conduit(s) can be located along an exterior of the handpiece 610 and/or any other portion of the assembly 600, as desired or required.

Regardless of the exact properties and details of the various components of an assembly's vacuum or suction system (including, e.g., the suction ports and/or passages 628, the suction conduit V and/or the like), once activated, the vacuum or suction system can be configured to generate, either intermittently or continuously, a vacuum force along the distal end of the tip 628. In some embodiments, such a vacuum force can help draw skin toward the tip 628, can facilitate with the delivery of fluids from the cartridge or other container 640 toward the skin and/or provide other benefits.

Figure 6B:
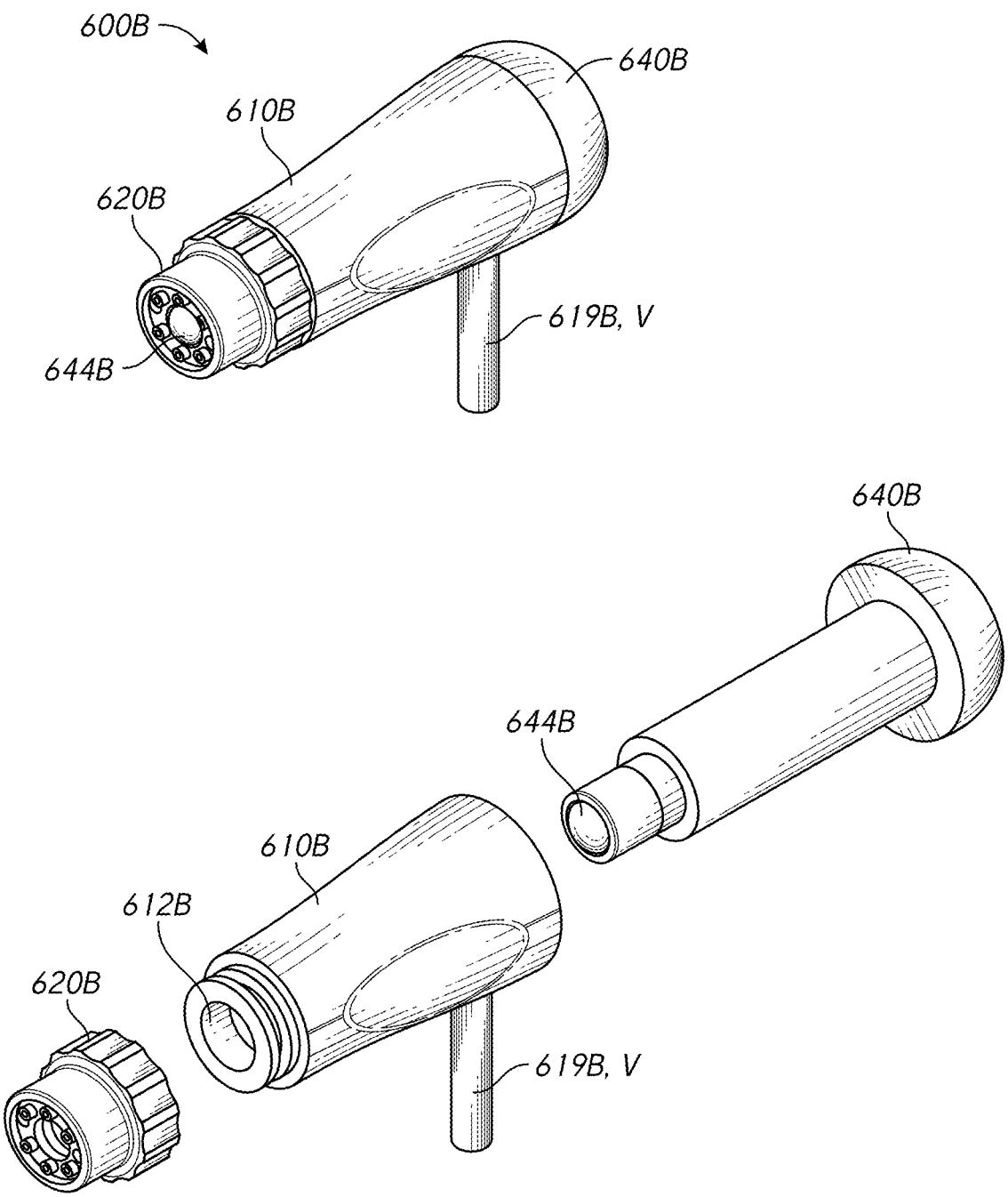
FIG. 6B illustrates perspective and corresponding exploded perspective views of an assembly comprising a rollerball for use with a skin treatment system according to one embodiment.

Another embodiment of an assembly 600B is illustrated in FIG. 6B. As shown, and similar to the embodiment of FIG. 6A, the depicted assembly 600B comprises a handpiece 610B that is configured to receive a tip 620B along its distal end. In some embodiments, the tip 620B can be removable from the handpiece 610B. However, the tip can be permanently or semi-permanently attached to the handpiece 610B (or can form a unitary or monolithic structure with the handpiece 610B). Further, as with other embodiments disclosed herein, a cartridge or other fluid source 640B can be configured to be secured within a portion (e.g., recess, cavity, etc.) of the handpiece 610B.

With continued reference to FIG. 6B, the distal end of the cartridge 640B can comprise one or more rollerballs 644B. In some embodiments, once properly secured to (e.g., within) the handpiece 610B, the distal end of the cartridge 640B and the rollerball 644B positioned on or near the distal end will extend to, near and/or through a central opening 612B along the distal end of the handpiece 610B. Likewise, the tip 620B can comprise an opening to permit the rollerball 644B to at least partially contact a subject's skin surface when the assembly 600B is moved relative to such a skin surface during use. For example, the tip 620B can include a central opening that is aligned with the rollerball 644B and provides direct access between the rollerball 644B and the distal end of the tip. Thus, as with other assembly arrangements disclosed herein, once the assembly 600B is moved along a subject's skin, the rollerball 644B can rotate to facilitate the delivery of fluids and/or other materials from the cartridge 640B to the tip 620B. For example, the rollerball 644B can be in fluid communication with one or more interior portions of the cartridge 640B.

According to some embodiments, the assembly 600B can be configured for the delivery of a vacuum or suction force along the tip 620B. As shown in FIG. 6B, the handpiece 610B can comprise a suction conduit 619B that extends from the exterior surface of the handpiece 610B and is configured to be placed in fluid communication with a vacuum source V (not shown). In some embodiments, however, as discussed herein with reference to FIG. 6A, for example, the suction or vacuum conduit or other hydraulic components can be routed through an interior of the handpiece 610B or other portion of the assembly 600B. For any of the embodiments disclosed herein or variations thereof, however, an assembly may not be configured for placement in fluid communication with a vacuum or suction source.

Figure 7:
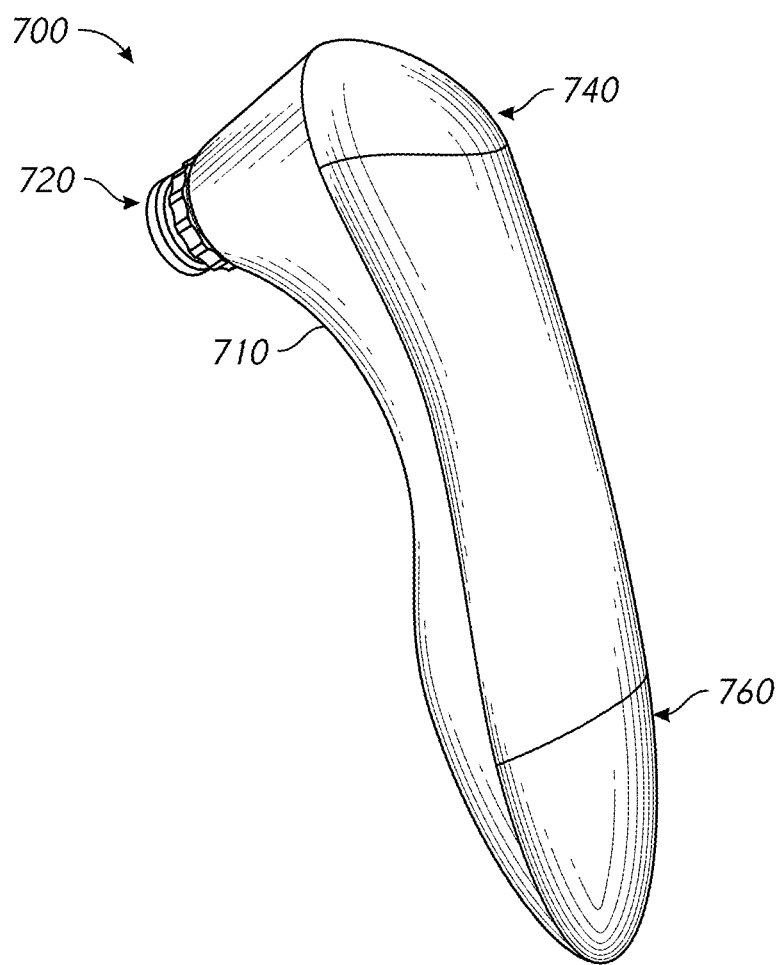
FIG. 7 illustrates a perspective view of an assembly comprising a rollerball for use with a skin treatment system according to one embodiment.

FIG. 7 illustrates another embodiment of a skin treatment assembly 700 comprising a rollerball to facilitate the delivery of fluids from a cartridge or other reservoir 740 to the tip 720 when the assembly 700 is moved relative to a subject skin surface. As shown, the assembly 700 can include a waste container or compartment 760 that is configured to receive any spent fluids and/or debris (e.g., exfoliated skin) that are removed from the tip 720. For example, in some embodiments, the waste container 760 can be in fluid communication with a vacuum or suction source to assist in drawing waste (e.g., spent fluids, exfoliated skin, other debris, etc.) away from the tip and the skin surface during a treatment procedure. Thus, as discussed with respect to other embodiments illustrated and described herein, one or more suction ports, passages, conduits, valves and/or other hydraulic components can be positioned between the tip and the waste container 760. In the arrangement illustrated in FIG. 7, the waste compartment is incorporated (e.g., removably) within the assembly 700. However, in other embodiments that include a suction or vacuum system, the waste can be delivered to a container, compartment or other collection point that is not incorporated within the assembly. For example, one or more vacuum conduits (e.g., tubing) can be used to deliver waste materials (e.g., exfoliated skin, spent fluids, etc.) to a separate container.

Figure 8:
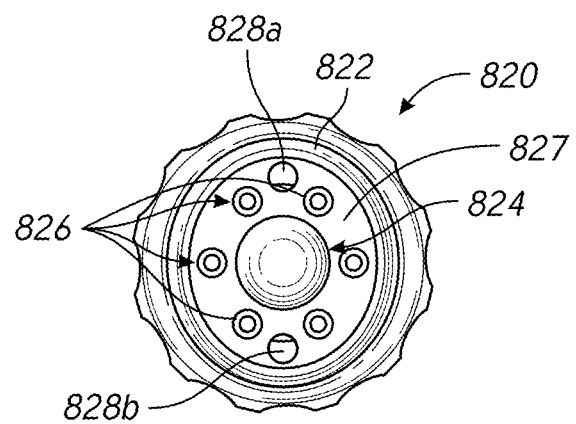
FIG. 8 illustrates a front view of a tip configured to be positioned along a distal end of an assembly disclosed herein, according to one embodiment.

FIG. 8 illustrates a front view of a tip 820 that is configured for use with one or more of the skin treatment assemblies disclosed herein or variations thereof. As with other arrangements illustrated and described herein, the tip 820 can include one or more rollerballs 824 that are configured to facilitate the delivery of fluids from a fluid source (e.g., a cartridge) to the tip and skin surface of the subject being treated when the assembly is moved relative to the subject's skin during use.

With continued reference to FIG. 8, the tip 820 can include a peripheral lip 822 that defines an interior region. In some embodiments, the lip 822 is sized, shaped and otherwise configured to contact the skin surface during use (e.g., whereas an interior region of the tip defined by the lip 822 is generally recessed relative to the distal end of the lip). As shown, the tip 820 can include one or more posts, other interior members and/or other abrading members or structures 826 (e.g., ridges, spiral-shaped members, other sharp surfaces, gritty or abrasive members, etc.) to help in the exfoliation of skin tissue as the tip is moved relative to a subject's skin. In some embodiments, however, the peripheral lip 822 can be configured to exfoliate skin tissue as the assembly is moved relative to a subject's skin surface during use, either in addition to or in lieu of any abrasive structures or members 826 positioned along an interior region of the tip 820.

With continued reference to FIG. 8, the tip can include one or more vacuum or suction ports 828a, 828b through which waste materials (e.g., spent fluids, exfoliated skin, other debris, etc.) can pass when the assembly's suction system is activated. The quantity, size, shape, spacing, orientation and/or other properties of the vacuum or suction ports 828a, 828b can be different than illustrated in FIG. 8, as desired or required by a particular design or application.

Further, as discussed in greater detail herein, the clearance or spacing between the rollerball 824 and the adjacent base surface 827 of the tip 820 can vary. For example, in some embodiments, such a clearance is about $1/128^{th}$ to $1/2$ inch. The rollerball 824 can be located within a housing that permits the rollerball to freely rotate and prevent the rollerball from being separated or otherwise removed from the tip during use. As noted herein, in some embodiments, the rollerball can be selectively removable from a particular housing of the tip, handpiece and/or cartridge (depending on which component of an assembly the rollerball is secured) for replacement, cleaning, maintenance and/or the like.

In any of the embodiments, disclosed herein, an assembly can include one, two or more rollerballs to facilitate the delivery or transfer of fluid from a cartridge, reservoir or other fluid source to the tip and the skin surface of a subject. The rollerball can be positioned along the longitudinal centerline of the assembly; however, in some arrangements, the rollerball is offset from the longitudinal centerline, as desired or required. Further, the rollerball can include one or more materials, such as, for example, metals or alloys (e.g., stainless steel, brass, titanium, etc.), thermoplastics and/or any other synthetic or natural material. The diameter (or other cross-sectional dimension) of the rollerball can be approximately $1/4$ inch to 2 inches. However, in other embodiments, the diameter or other cross-sectional dimension of the rollerball, wicking member and/or other member positioned along the distal end of a handpiece can be smaller than $1/4$ inches or greater than 2 inches, as desired or required.

According to some embodiments, the rollerball can include a solid (e.g., non-porous) structure or a porous structure, as desired or required. In any of the embodiments disclosed herein, the rollerball can include one or more coatings or other materials. For example, the rollerball can include one or more layers of dissolvable materials that are configured to dissolve and thus be released to the skin surface being treated in the presence of water or another diluting agent. In some arrangements, a rollerball comprises a porous structure that is at least partially saturated with one or more substances that are configured to be released (e.g., dissolve) during use. Such materials can be located, at least initially, within an interior portion of the rollerball. As discussed herein, the rollerball can be included in a system that is configured to generate a vacuum or suction at or near the tip, thereby enhancing the effect of using a rollerball or similar structure to engage targeted skin and/or delivery fluids to the skin surface. Further, the rollerball can be positioned adjacent a wicking member, porous member and/or other member that is configured to retain liquid. This can assist in ensuring that the rollerball maintains a certain degree of moisture, regardless of whether liquid would be otherwise immediately present at or near the rollerball.

In any of the embodiments disclosed herein, the rollerball and/or wicking member can comprise one or more abrasive and/or other roughened or sharp surfaces or features. Such embodiments can facilitate exfoliation of skin as the handpiece is moved along a subject's skin surface.

Another embodiment of a skin treatment assembly 900 comprising a rollerball is illustrated in FIGS. 9A and 9B. Unlike other arrangements disclosed herein, the depicted assembly 900 includes a handpiece and a tip that are integrated into a single unitary or monolithic structure 910. In some embodiments, such a combined handpiece and tip can be configured to be disposable so it is replaced between uses. According to some embodiments, the assembly 900 comprises a cartridge or other fluid source 940 that is configured to secure to the combination handpiece/tip 910.

With continued reference to FIG. 9B, the distal end 942 of the cartridge 940 can include a rollerball 944 that is routed through an interior portion of the combination handpiece/tip 910 when the cartridge 940 is positioned therein. In some embodiments, the rollerball 944 extends to or near the distal end of the combination handpiece/tip 910 when the assembly 900 is ready for use. Accordingly, as the assembly 900 is moved relative to a subject's skin surface, the rollerball can at least partially contact the skin surface being treated and rotate. Rotation of the rollerball 944 can facilitate the transfer of fluid and/or other contents of the cartridge 940 to the distal end of the combination handpiece/tip 910, and thus, the skin surface.

As shown in FIGS. 9A and 9B, the proximal end 945 of the cartridge 940 can include a closure member 946 that sealingly encloses an interior of the cartridge 940. Thus, in some embodiments, the interior of the cartridge 940 can be opened, refilled and closed. However, in other arrangements, the cartridge 940 is configured to remain sealed at all times. Thus, is such configurations, the cartridges are disposable after use. The above disclosure regarding cartridges that can be opened and cartridges that are configured to remain sealed can be applied to any of the assembly arrangements disclosed herein or variations thereof.

As discussed above with reference to other embodiments, the cartridge 940 included in the assembly 900 of FIGS. 9A and 9B can be re-used between sequential treatment procedures. For example, once the subject has completed a particular treatment session, the subject can be permitted to take home any used cartridge or cartridges (to the extent two or more different serums or other treatment materials were used). Thus, the subject can bring the unused cartridges to a subsequent treatment session, thereby eliminating waste and reducing the overall expense of a procedure. In some embodiments, the subject can be instructed to apply one or more of the serums and/or other materials contained within the corresponding unused cartridges 940 to his or her skin between office visits. Accordingly, in order to prevent contamination of the cartridges and their internal contents, to prevent evaporation, leaks or other loss of the internal contents of the cartridges, to otherwise protect the cartridges (e.g., the rollerball 944 located along the cartridge's distal end) and/or to provide one or more additional benefits or advantages, a cap 950 can be used to protect the distal end 942 of a cartridge between uses. The rollerball 944 can facilitate the application of fluid to the subject's skin surface between office visits. For example, the use of a rollerball can advantageously permit fluid to be delivered from the interior of the cartridge 940 to the subject's skin surface without the use of suction or a handpiece. Thus, the overall effectiveness of a skin treatment procedure can be advantageously enhanced by such embodiments.

In some embodiments related to the treatment of acne, for example, two main serums or materials can be used during a treatment procedure. Thus, during a first visit to a professional, the subject undergoes a two-step treatment procedure in which an acidic formulation (e.g., salicylic acid) is first applied to the subject's skin surface (e.g., with or without the application of vacuum) to remove impurities and clear out the subject's pores. As a follow-up step, an antibiotic or other treatment serum is applied to the skin. In some embodiments, as discussed herein, the user is then provided with cartridges or other fluid containers. Such cartridges can be advantageously returned to the professional for conducting a follow-up procedure during a subsequent visit. In addition, the subject can be instructed, in accordance with certain protocols, to periodically apply one or more of these serums or fluids to his or her skin between visits, as desired or required.

As noted above, the combination handpiece/tip 910 included in the assembly of FIGS. 9A and 9B can be disposable between uses or sequential procedures. Thus, the use of such a disposable portion can reduce the likelihood of the transfer of contamination between subjects and/or procedures, thereby improving the overall hygiene and safety of skin treatment procedures.

With continued reference to FIGS. 9A and 9B, the combination handpiece/tip 910 can include a suction port or conduit 918 that is configured to be placed in fluid communication with a vacuum source. In the illustrated embodiment, suction port 918 extends along an exterior of the handpiece/tip component 910 (e.g., at an angle); however, in other arrangements, the suction port or conduit 918 can extend, at least partially or completely, within an interior of the assembly 900, as desired or required. In yet other embodiments, the assembly 900 is not configured to be placed in fluid communication with a suction or vacuum source. Accordingly, in such arrangements, the assembly need not have any suction or vacuum ports, passages, conduits and/or other related components or features.

In any of the embodiments disclosed herein, including those illustrated in FIGS. 1-9B, the rollerball or similar feature along the distal end of a cartridge, handpiece and/or tip can be replaced with one or more other features that to help to selectively deliver fluid to the skin surface being treated (e.g., from a reservoir of a cartridge or other container placed in fluid communication with the system). For example, as illustrated in the embodiment of FIG. 10, the rollerball can be replaced with a wicking or other fluidly porous member 1044 along its distal end.

Figure 10:
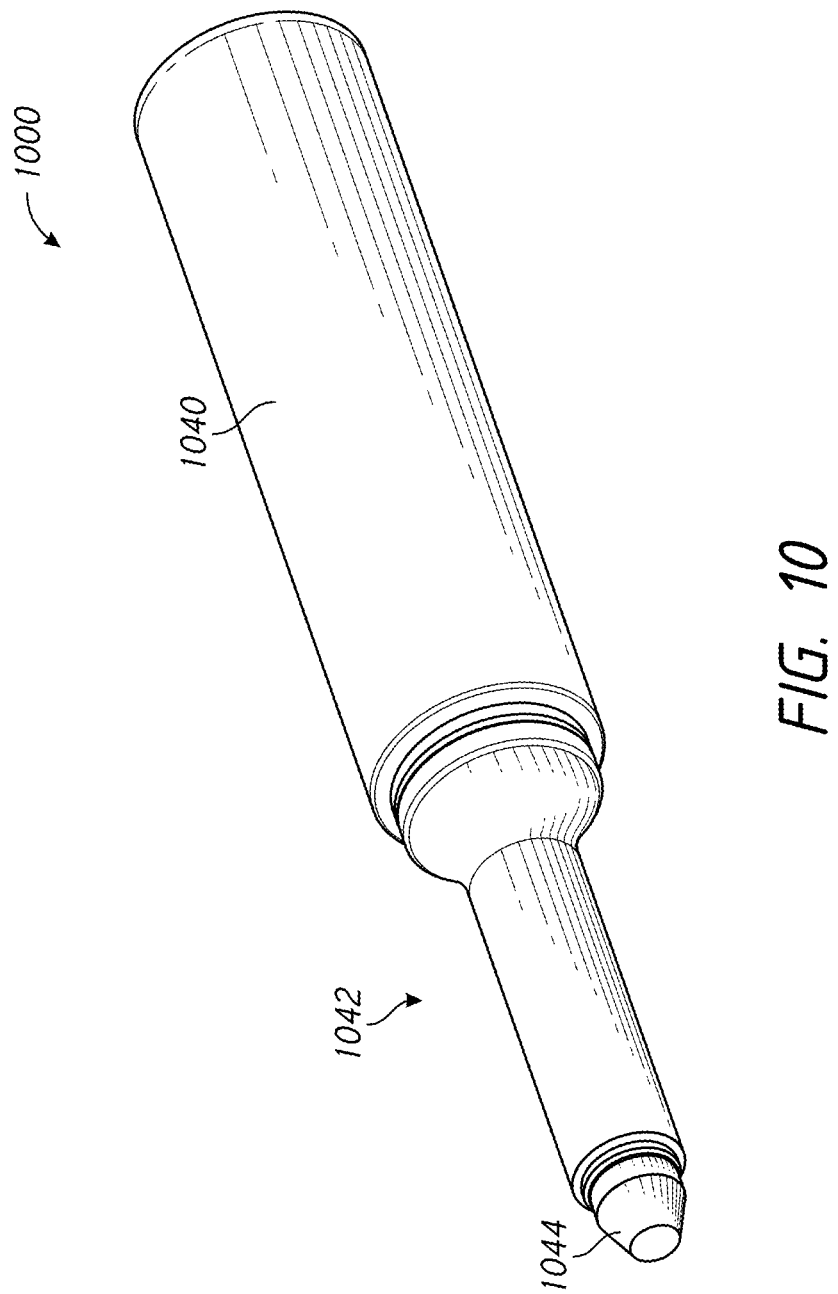
FIG. 10 illustrates a perspective view of an assembly comprising a wicking member for use with a skin treatment system according to one embodiment.

With reference to FIG. 10, the distal end 1042 of the cartridge 1040 can include a wicking member or other porous member 1044. In some embodiments, the rollerball 944 extends to or near the distal end of the combination handpiece/tip when the assembly is ready for use. Accordingly, as the assembly is moved relative to a subject's skin surface, the wicking member 1044 can at least partially contact the skin surface being treated and deliver fluid from the fluid reservoir of the cartridge or other container 1040 to the skin surface. The wicking member 1044 can comprise one or more porous materials or features, such as, for example, foam, a porous stone, sponge or other member, another material or member comprising a porous or otherwise open or semi-open structure. In some embodiments, the wicking or other porous member 1044 can be saturated with the particular fluids contained within the reservoir of the cartridge or other container member. Thus, the wicking member 1044 can retain the necessary moisture level to selectively deliver fluid to the skin surface treated, even when the level of fluid within the cartridge or the other container 1040 is relatively low.

With continued reference to FIG. 10, the wicking member 1044 can comprise one or more foams, thermoplastics and/or other materials. The cross-sectional size of the wicking member can be between ¼ inch and 2 inches. In some embodiments, the wicking member 1044 extends, at least partially, within the interior reservoir of the cartridge or other container. The wicking member 1044 can include any cross-sectional shape, as desired or required, such as, for example, circular, oval, square or other rectangular, other polygonal (e.g., triangular, pentagonal, hexagonal, octagonal, decagonal, etc.), irregular.

Figure 11:
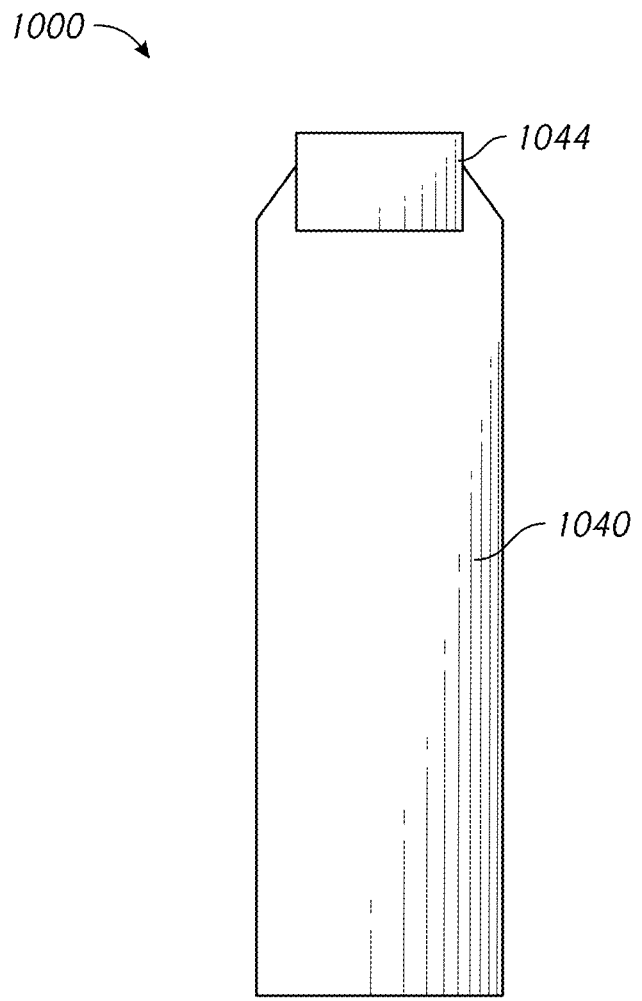
FIG. 11 schematically illustrates a side view of an assembly comprising a wicking member for use with a skin treatment system according to one embodiment.

FIG. 11 schematically illustrates a skin treatment system 1000 similar to the system depicted in FIG. 10. As shown, the system 1000 can include a cartridge or other container 1040 comprising a wicking or other porous structure 1044 along its distal end. The wicking or other porous structure can include one or more materials that are configured to at least partially absorb, adsorb and/or otherwise retain a volume of liquid or other material. As discussed herein, according to some embodiments, such a wicking structure 1044 can be used to keep the distal end of the cartridge 1040 at least partially moist for purposes of delivering fluids and/or other materials to the skin surface of a subject during a particular procedure.

According to some embodiments, the wicking or other porous structure 1044 incorporated into any of the embodiments herein (e.g., the distal end of a cartridge or other container, the handpiece, the tip, etc.) can be used for one or more purposes. For example, in some embodiments, the wicking material can be used to perform one or more of the following functions: (i) to store one or more materials within a portion of a skin treatment assembly (e.g., along a distal end of a cartridge, along a tip of an assembly, along a handpiece, etc.); (ii) as a filter (e.g., for waste debris leaving the skin surface being treated); (iii) for delivering fluids and/or other materials to the skin surface being treated; and/or the like. For example, in one embodiment, a wicking or other porous material 1044 can include a treatment material (e.g., as a liquid, gel, powder, etc.). Water or another dilution agent can then be delivered to or near the wicking or porous member 1040 to selectively release the materials stored within the wicking or other porous member.

Figure 12:
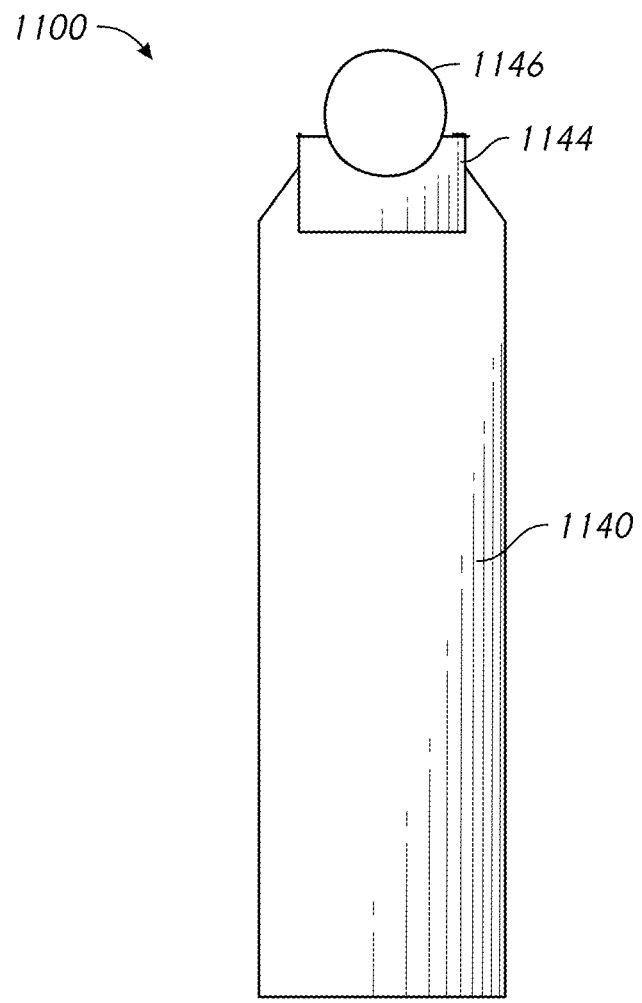
FIG. 12 schematically illustrates a side view of an assembly comprising a wicking member and a rollerball for use with a skin treatment system according to one embodiment.

According to some embodiments, as schematically illustrated in FIG. 12, a rollerball or other movable member 1146 can be positioned along the distal end of a wicking or other porous member or structure 1144. In such a system 1100, the wicking member 1144 and rollerball 1146 can be positioned along the distal end of a cartridge 1140. Alternatively, as with other configurations disclosed herein, the wicking member 1144 and/or the rollerball 1146 (or combination thereof) can be located along the handpiece, the tip and/or any other location of the skin treatment assembly. In such embodiments, the rollerball 1146 can be kept in fluid communication with the fluid contained within the cartridge or other container with the assistance of the wicking member or structure. In other words, the proximal end of the rollerball can be advantageously maintained moist with the assistance of the wicking material. Thus, for example, if the handpiece is being handled such that the liquid would be away from the rollerball 1146, the wicking or porous member helps to ensure that a certain degree of liquidity or moisture is maintained adjacent the rollerball or other movable member. This can help promote a more consistent application of liquid to the skin surface.

Figure 13A:
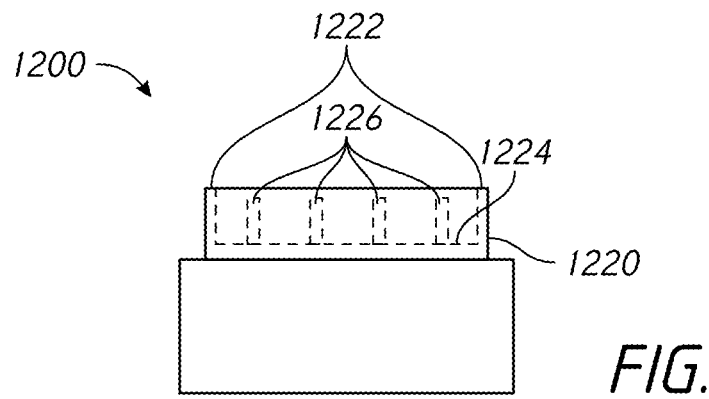
FIG. 13A schematically illustrates a side view of an embodiment of a tip configured to be positioned along a distal end of a skin treatment assembly.

FIG. 13A illustrates schematically a tip 1200 that is configured to be positioned along the distal end of a skin treatment system. As shown and discussed in greater detail in one or more applications incorporated by reference herein, the tip 1200 can include a peripheral lip 1222 that is configured to contact skin tissue and form a seal during use (e.g., to help deliver fluids to the skin surface upon the application of vacuum or suction to the assembly). With continued reference to FIG. 13A, the tip 1200 can also include a recessed base 1224 from which one or more abrading members or structures 1226 extend. For example, such abrading members or structures can include one or more posts, spiral ridges and/or the like. Regardless of their exact shape, structure and/or other properties, such abrading members or structures 1226 can include a sharp or abrading edge or structure to facilitating the abrasion of skin tissue during use.

Figure 13B:
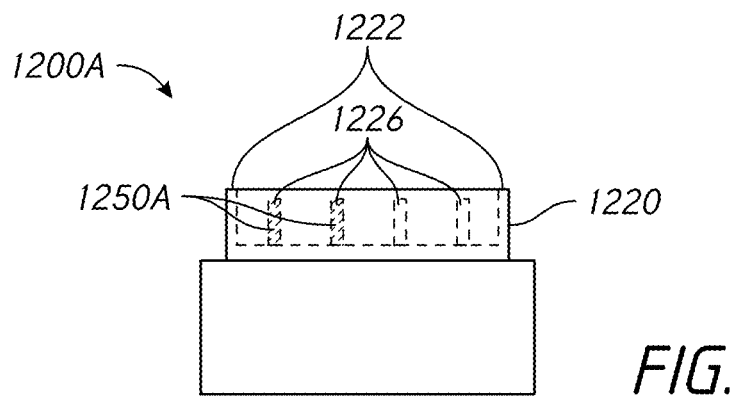
FIGS. 13B to 13D illustrates different embodiments of the tip of FIG. 13A having a wicking or other porous material positioned on and/or along one or more tip portions.
Figure 13C:
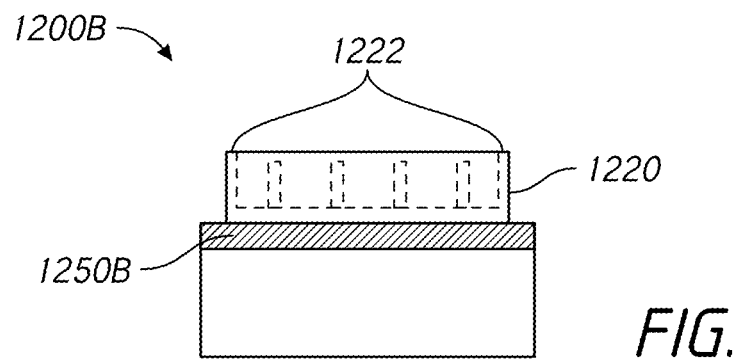
Figure 13D:
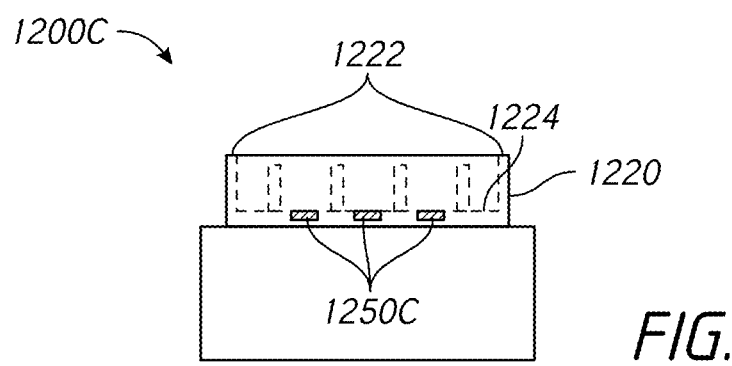

As shown schematically in FIGS. 13B to 13D, one or more wicking or porous structures or members 1250 can be advantageously positioned along, near or within a portion of the tip 1200. Such wicking or porous members 1250A, 1250B, 1250C can include within their structures one or more materials that are intended to be released to the skin surface during use (e.g., when a dilution agent is delivered to the tip). For example, as shown in FIG. 13B, the wicking or porous member 1250A can be positioned along one or more posts or other protruding members 1226 of the tip. In other embodiments, as shown in FIG. 13C, the wicking or porous member can be positioned along the underside of the base 1224, but can still be in fluid communication with a dilution agent (e.g., water) that is selectively delivered to the tip. In such arrangements, the wicking member 1250B can comprise a disk or other component that fits within or other portion of the tip (e.g. friction fit, using one or other fasteners or other retaining members, etc.). In yet other embodiments, as shown in FIG. 13D, the wicking member 1250C can be positioned along one or more recesses of the base 1224 and/or other portion of the tip 1200.

Figure 14:
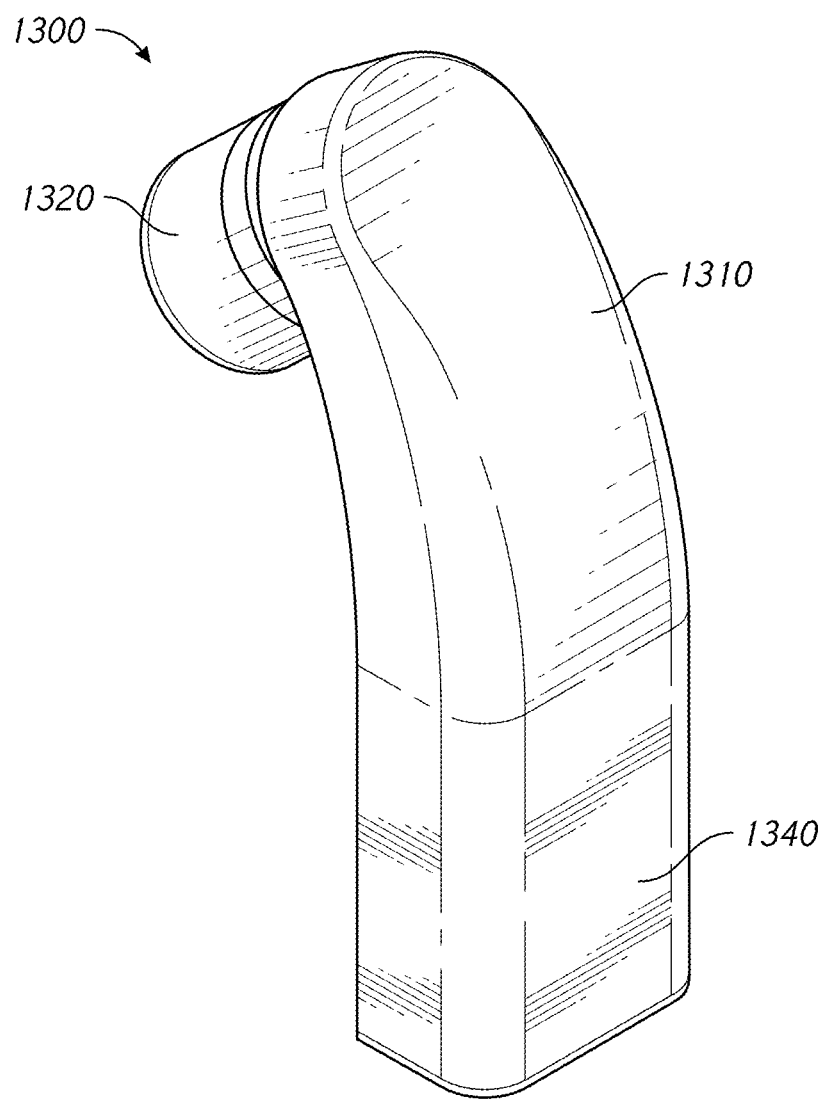
FIG. 14 illustrates a perspective view of one embodiment of a skin treatment assembly comprising fluid supply and waste containers attached along the proximal end of the assembly.

FIG. 14 illustrates a perspective view of a skin treatment assembly 1300 that comprises a unitary structure 1340 along its proximal end that is configured to releasably secure to a proximal handpiece portion 1310. In some embodiments, such a unitary structure 1340 comprises one or more compartments or portions. For example, one compartment or portion of the structure 1340 can be used to store a fluid or other treatment material that is intended to be selectively delivered to a skin surface via the handpiece 1310 and the distal tip 1320. Further in some embodiments, the structure 1340 can include one or more additional compartments or portion. In one embodiment, for instance, such an additional compartment can include a waste compartment that is configured to receive spend fluids, abraded skin and/or other debris removed from the skin surface being treated. Additional details regarding such assemblies are provided in U.S. Pat. No. 8,343,116, filed as U.S. patent application Ser. No. 12/346,582 on Dec. 30, 2008 and issued on Jan. 1, 2013.

Figure 15:
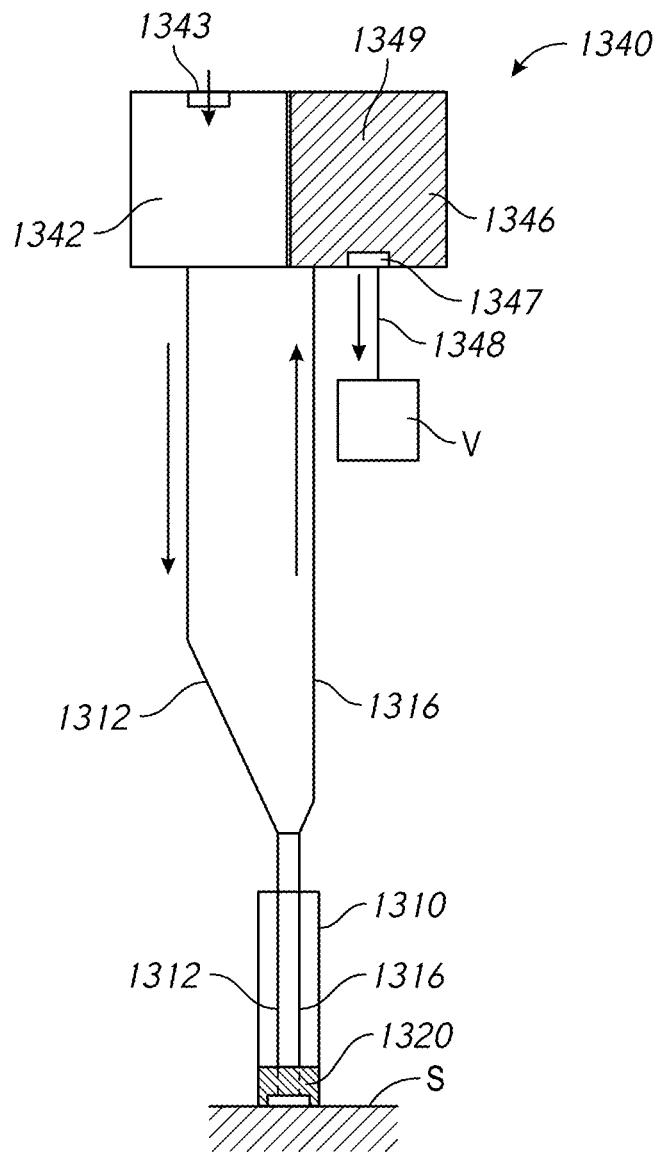
FIG. 15 schematically illustrates a skin treatment system similar to the system depicted in FIG. 14.

FIG. 15 schematically illustrates one embodiment of an assembly similar to the one discussed herein with reference to FIG. 14. As shown, in some embodiments, a wicking materials or other porous structure 1349 can be positioned along the interior of the waste compartment 1346 of a unitary structure 1340. The wicking or other porous structure can help absorb the waste materials within its structure to facilitate the use of a handheld device, especially one (like in FIG. 14) that incorporates a waste structure at its proximal end. In other words, the wicking material 1349 can help ensure that the waste fluids and/or other waste materials do not disadvantageously move within the compartment 1346 during use. In addition, such a configuration can assist with the removal and/or disposal of the waste contents from the waste compartment. For example, in some embodiments, the wicking and/or other porous member can be easily removed and discarded without having to deal with loose fluids.

In some embodiments, as illustrated schematically in FIG. 15, a hydrophobic member 1343, 1347 can be advantageously placed along a portion of the fluid retention compartment 1342 and/or the waste compartment 1346 to facilitate the passage of air into and/or out of the compartments 1342, 1346 during use. For example, such members 1343, 1347 can act as one way valves that permit air to pass therethrough (e.g., to prevent or reduce the likelihood of vacuum forces from forming within the respective compartments), while not allowing liquids and/or other materials from passing.

According to some embodiments, the various systems disclosed herein can be used to treat one or more skin conditions of a subject. For example, the systems can be used to target the following conditions/target treatments: acne, skin lightening, skin tightening, anti-aging, oily skin, lip repair/plumping and/or the like. Example treatment protocols for at least some of the conditions/target treatments are provided below. For example, in some arrangements, protocols identical or similar to those provided in Table A below can be used.

TABLE A

| Protocol/Procedure | Step 1 Fluid Active Ingredients | Step 2 Fluid Active Ingredients | Step 3/4 Fluid active ingredients |
|---|---|---|---|
| Acne | Preparatory/Exfoliating agent with salicylic acid or other agent that will breakdown oils and dead tissues on the surface layers of the skin | Treatment agent (e.g., anti-oxidants, silver, in combination with one or more agents such as benzyl peroxide, Salicylic acid or sulfur. | A treatment agent consisting of oil free moisturizing agents combined or applied separately with agents to block UV rays and other oxidizing elements. |
| Skin lightening | Preparatory/Exfoliating agent with salicylic acid or other agent that will breakdown oils and dead tissues on the surface layers of the skin | A treatment agent consisting of but not limited to, *avena sativa* (oat) kernel extract, Palmaria palmatate, horsechest nut and green tea extract. | A treatment agent consisting of moisturizing agents combined or applied separately with agents to block UV rays and other oxidizing elements. |
| Skin tightening | Preparatory/Exfoliating agent with salicylic acid or other agent that will breakdown oils and dead tissues on the surface layers of the skin. | A treatment agent consisting of but not limited to, *avena sativa* (oat) kernel extract, Palmaria palmatate, horsechest nut and green tea extract. | A treatment agent consisting of moisturizing agents combined or applied separately with agents to block UV rays and other oxidizing elements. |
| Anti-aging | Preparatory/Exfoliating agent with salicylic acid or other agent that will breakdown oils and dead tissues on the surface layers of the skin. | A treatment agent consisting of but not limited to transdermal application of antioxidants, such as but not limited to, lipoic acid bioflavonoid, (*aesculus hippocastanum*) horse chestnut, proanthocyanidin and a mixture of amino acids combined with sulfur and or benzyl alcohol or other penetrant enhancers. | A treatment agent consisting of moisturizing agents combined or applied separately with agents to block UV rays and other oxidizing elements. |
| Oily skin | Preparatory/Exfoliating agent with salicylic acid or other agent that will breakdown oils and dead tissues on the surface | Treatment agent (e.g., anti-oxidants, silver, in combination with one or more agents | A treatment agent consisting of oil free moisturizing agents combined |

TABLE A-continued

| Protocol/Procedure | Step 1 Fluid Active Ingredients | Step 2 Fluid Active Ingredients | Step 3/4 Fluid active ingredients |
|---|---|---|---|
| | layers of the skin | such as benzyl peroxide, Salicylic acid or sulfur. | or applied separately with agents to block UV rays and other oxidizing elements. |
| Lip Repair/Plumping | Preparatory/Exfoliating agent with salicylic acid or other agent that will breakdown oils and dead tissues on the surface layers of the skin | Treatment agent (e.g., anti-oxidants and collagen building Ingredients such as but limited to amino acids such as palmitoyl dipeptide-10, palmitoyyl dipeptide-1,7, palitoyl hexipeptide-12. | A treatment agent consisting of moisturizing agents combined or applied separately with agents to block UV rays and other oxidizing elements. |
| Anti-oxidant/growth factor treatment | Preparatory/Exfoliating agent with salicylic acid or other agent that will breakdown oils and dead tissues on the surface layers of the skin | Apply Epicatechin (e.g., synthetic and/or naturally derived) and/or other growth factor(s). In some embodiments, allow sufficient time to dry before continuing to the next step. In some arrangements, Epicaeichin could be in a powder form that needs to be mixed just prior to application | Antioxidant(s) and/or other agents. In some embodiments, the process can include the application of additional agents, such as, e.g., sunscreen(s), as a follow up step. In one embodiment, the sunscreen can be 30SPF or greater |

According to some embodiments, with reference to the Epicatechin treatment listed above can be included in a take home unit, as described in greater detail herein. In some embodiments, the Epicatechin product is applied daily morning and/or night. The Epicatechin could be provided in the form of a lotion, cream or serum, wax lipstick delivery medium and/or the like. In some embodiments, antioxidant product(s) is/are applied daily morning and/or night. Like the Epicatechin product, antioxidants could be provide as a lotion, cream or serum, wax lipstick delivery medium and/or the like, as desired or required.

For example, as indicated in Table A above, in some embodiments, the initial step of a treatment protocol comprises one or more preparatory steps or procedures. For example, in some arrangements, the subject's skin is initially exfoliated, at least partially, regardless of the exact protocol being used. In some configurations, salicylic acid or other agent that will breakdown oils and dead skin tissue on the surface layers of the subject's skin can be selectively delivered to the skin of a subject. The delivery of such preparatory fluids can be performed using a device disclosed herein (e.g., a vacuum-assisted assembly). Alternatively, such materials can be delivered to the skin surface using one or more other methods or devices (e.g., topically applied without the use of separate device). In some embodiments, the delivery of fluids while suction is applied to the skin (e.g., via a suction-enabled assembly) can facilitate the delivery of fluids below the outermost surface of the skin to thereby enhance the initial preparatory step of a procedure or protocol.

With further reference to Table A, as a second step to a treatment procedure, a first treatment agents or combination of treatment agents (e.g., anti-oxidants, silver, benzyl peroxide, salicylic acid, sulfur, *Avena sativa* (oat) kernel extract, palmaria palmatate, horsechest nut, green tea extract, lipoic acid bioflavonoid, (*Aesculus hippocastanum*) horse chestnut, proanthocyanidin and a mixture of amino acids combined with sulfur and or benzyl alcohol or other penetrant enhancers and/or the like can be delivered to the skin via the rollerball, wincing material and/or the like.

Further, with continued reference to Table A, as a third step to a treatment procedure, a second treatment agents or combination of treatment agents (e.g., anti-oxidants, silver, benzyl peroxide, salicylic acid, sulfur, *Avena sativa* (oat) kernel extract, *Palmaria palmatate*, horsechest nut, green tea extract, lipoic acid bioflavonoid, (*Aesculus hippocastanum*) horse chestnut, proanthocyanidin and a mixture of amino acids combined with sulfur and or benzyl alcohol or other penetrant enhancers and/or the like can be delivered to the skin via the rollerball, wincing material and/or the like.

Figure 16:
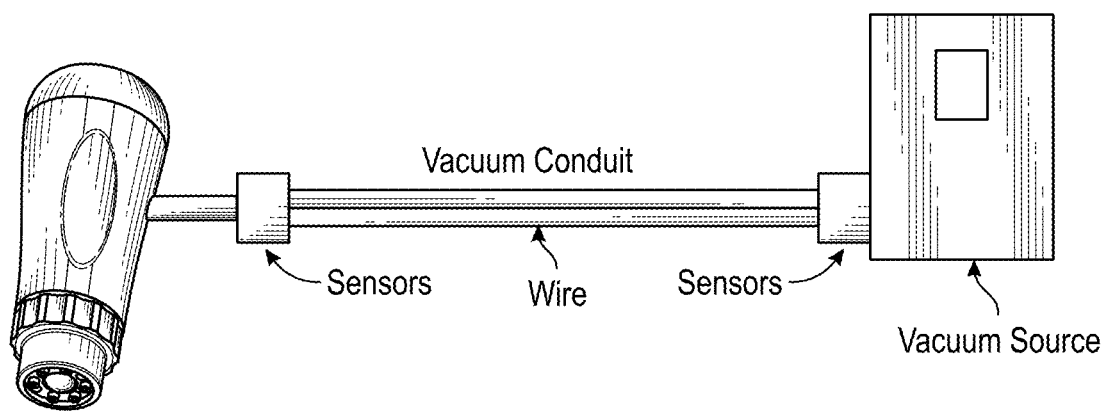
FIG. 16 illustrates one embodiment of a system comprising a vacuum source that is in fluid communication with a handpiece or other skin treatment device.
Figure 18:
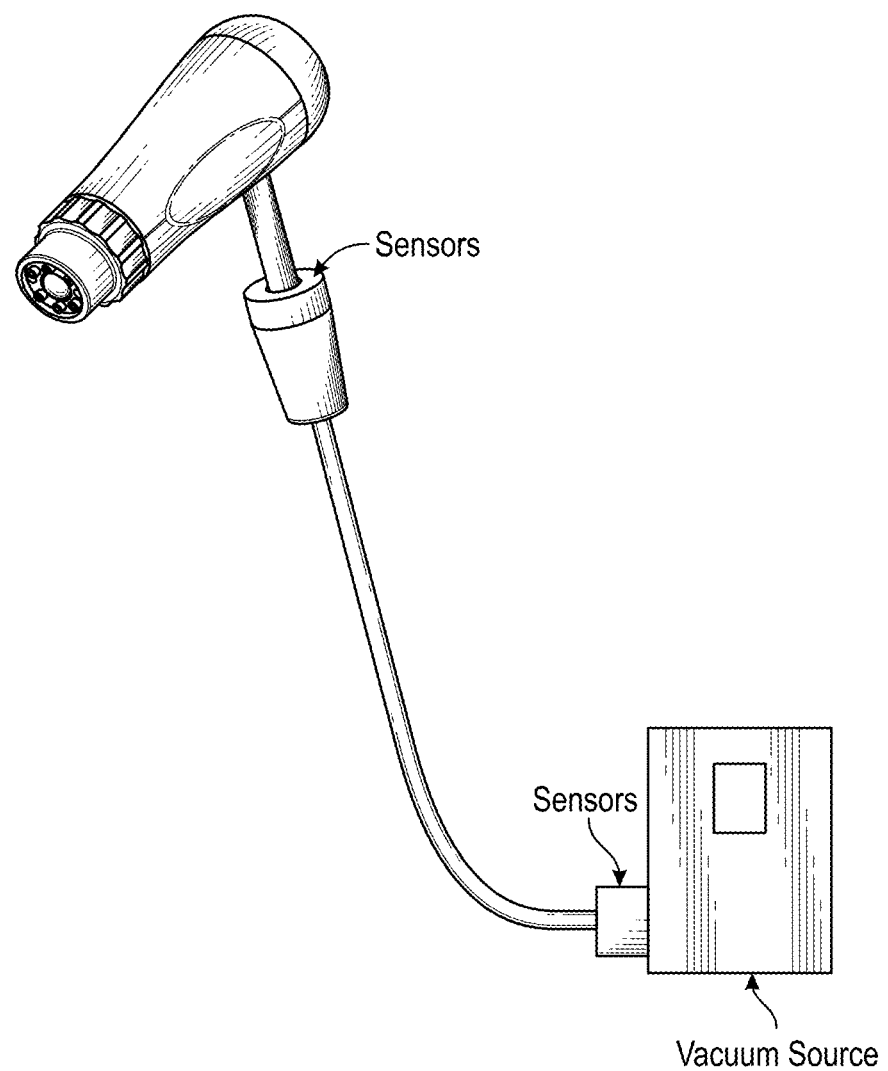
FIG. 18 illustrates one embodiment of a skin treatment system comprising sensors along or near opposite ends of a vacuum conduit that places a skin treatment member in fluid communication with a vacuum source.

FIGS. 16 and 18 schematically illustrate different embodiments of a system having a handpiece or other skin treatment component configured to contact skin along one end. As discussed herein, such a handpiece or other component can comprises a rollerball, wicking members and/or the like. As shown in FIGS. 16 and 18, a conduit (e.g., vacuum tubing) can be used to place the handpiece or other treatment component in fluid communication with a vacuum source (e.g., a vacuum unit). In some embodiments, one or both ends of the conduit can include a sensor to ensure that a satisfactory connection is made with the handpiece and the vacuum source before the system can be activated. One or more wires, conduits, cables and/or other electrical connections can be included in the system to facilitate the necessary connection to the sensor(s) and/or other electrical components. In other embodiments, the necessary electrical and/or data connections are wireless (e.g., Bluetooth). Regardless of the exact configuration, such handpiece sensing features can permit the system to operate when the electrical and/or date circuit is completed.

Figures 17A, 17B:
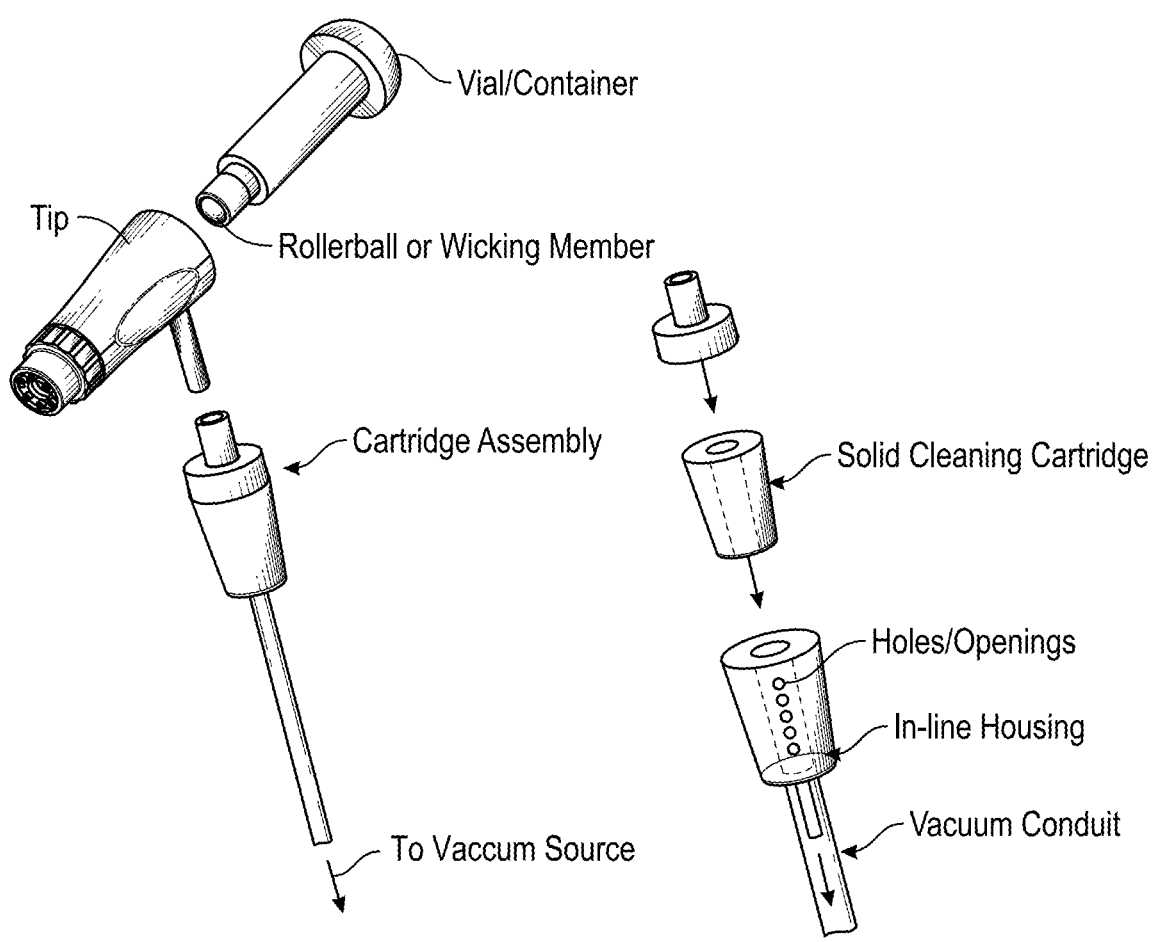
FIGS. 17A and 17B illustrate different exploded views of a system comprising cartridge assembly located between the skin treatment device and a vacuum source according to some embodiments.

FIGS. 17A and 17B illustrates different embodiments of systems that comprise a cartridge assembly that is configured to at least partially absorb and/or otherwise retain waste material being removed from the skin (e.g., spent serums and/or other treatment materials, exfoliated skin, other debris, etc.). For example, in one embodiment, a cartridge assembly that is in fluid communication with a vacuum source, as depicted in FIG. 17B, can be sized, shaped and/or otherwise configured to receive a removable solid cleaning cartridge. Such a removable cartridge can be advantageously removed, discarded and replaced, thereby reducing exposure of waste materials during routine maintenance, cleaning and/or other normal operation of the system. As shown, the receptacle into which the solid cleaning cartridge is placed can include a central conduit having a plurality of openings, pores and/or the like that place the central conduit in fluid communication with the removable cartridge. In some embodiments, as discussed in greater detail herein, such a cartridge can comprise a porous, wicking, absorptive and/or other material configured to at least partially receive and/or retain fluids and/or other materials.

FIG. 18 schematically illustrates one embodiment of a system that comprises sensors along both the handpiece and the vacuum source to ensure proper connection of conduits of the system. In some arrangements, the sensors can help identify the components that are used in the system. This can provide a level of security that the components are intended to be used with one another, and that no unintended components that can interfere with the proper function of the system are included in a particular arrangement.

Figure 19A:
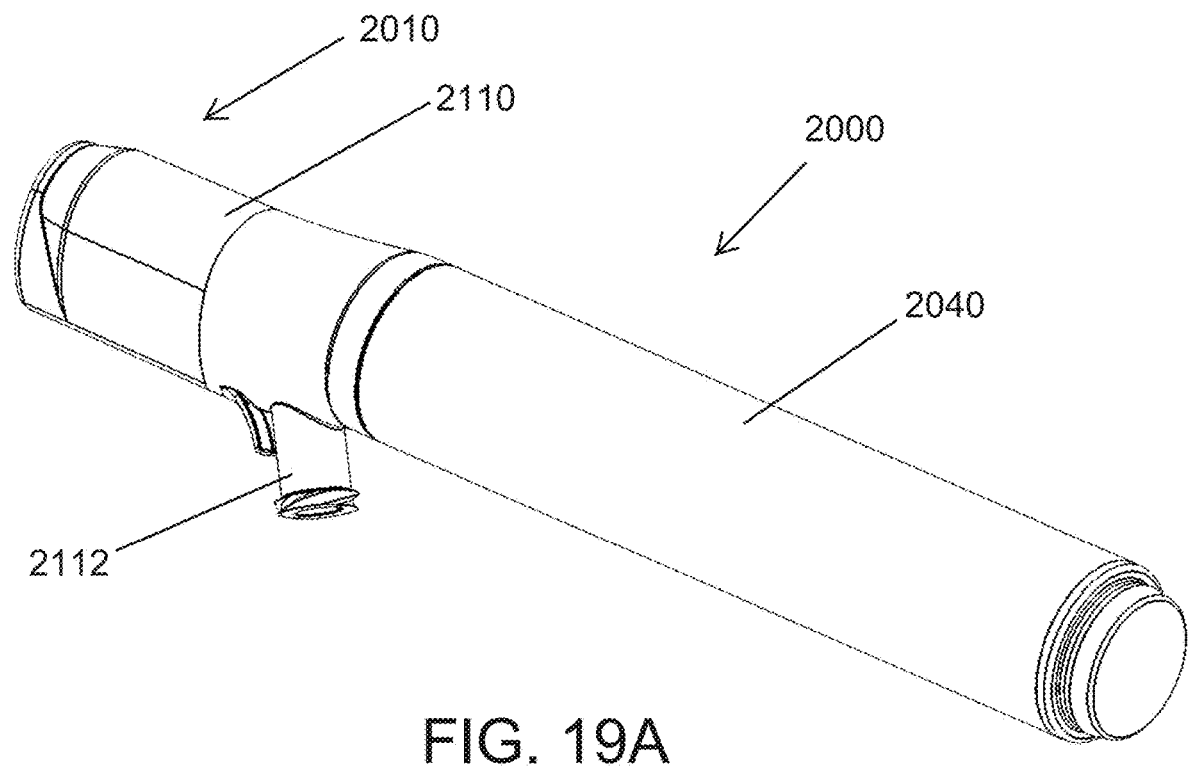
FIGS. 19A and 19B illustrate different perspective views of an assembly comprising a rollerball for use with a skin treatment system according to another embodiment.
Figure 19B:
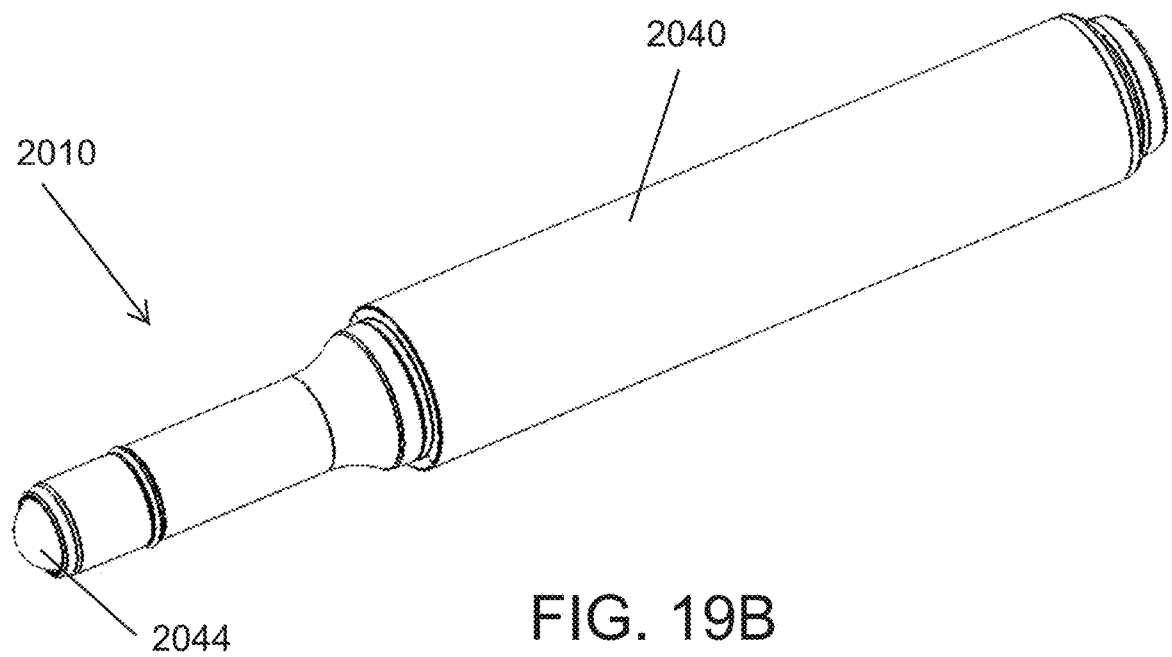

FIGS. 19A and 19B illustrate different views of yet another embodiment of a skin treatment assembly 2000 comprising a rollerball (and/or another porous, wicking, other absorbent material or member, and/or the like) 2044 along its distal end 2042. As with other embodiments disclosed herein, the rollerball or other member positioned along the distal end 2044 can facilitate delivery of fluids and/or other materials to a subject being treated with the assembly 2000. In some embodiments, as illustrated in FIG. 19A, the assembly 2000 can include a cartridge or other container 2040. Further, the distal end 2010 of the assembly 2000 can include a handpiece portion 2110 that is sized, shaped and/or otherwise adapted to secure to the distal end of the cartridge 2040.

With continued reference to FIG. 19A, the handpiece portion 2110 can be configured to fit over the distal end of the cartridge or other container 2040 such that a rollerball or other member (e.g., wicking member, porous member, absorptive member, etc.) 2040 located along the distal end of the container 2040 can extend to the distal end of the assembly 2000. For example, in some embodiments, such a rollerball or other member 2044 can form the most distal surface of the assembly once the handpiece portion 2110 is secured to the cartridge or other container 2040. In other embodiments, however, the distal end of the rollerball or other member that is configured to facilitate delivery of fluid(s) to the skin surface of a subject is aligned with, generally aligned with or proximal to another portion of the handpiece assembly 2110 and/or another portion or component of the assembly 2000, as desired or required. Thus, in some configurations, the assembly 2000 relies, at least in part, on suction or vacuum created along the distal end of the assembly to draw the targeted skin surface toward (e.g., adjacent to, in contact with, etc.) the rollerball and/or other distal member 2044, as desired or required.

As discussed with respect to other embodiments herein, the use of vacuum or suction to help draw the tissue toward the rollerball or other distal member (e.g., wicking member, porous member, absorptive member, etc.) can help enhance a skin treatment procedure. For example, the ability to selectively delivery fluids and/or other substances or materials (e.g., included within the cartridge or other container that is physically coupled to and/or in fluid communication with a container, e.g., a multi-container manifold system) can be improved and/or otherwise enhanced by the use of suction or vacuum. For example, the application of a vacuum or suction force along the tip can help deliver fluids and/or other substances to the skin surface being treated at a controlled rate of delivery. This can be contrasted with embodiments that rely only on gravity to deliver fluids and/or other materials to the skin surface. The use of a vacuum or suction force (e.g., once a seal has been created between a distal lip or periphery of a tip or other distal portion of an assembly, in accordance with various embodiments disclosed herein), can help ensure that fluid and/or other materials contained within a container (e.g., cartridge) and/or other fluid system with which the assembly 2000 is in fluid communication (e.g., a manifold system) is consistently and adequately delivered to the targeted skin surface. This is applicable to and may be specifically adapted for any of the embodiments disclosed herein.

With continued reference to FIG. 19A, the handpiece portion 2110 of the assembly 2000 can include a port 2112 that is adapted to be coupled to a vacuum or suction source. In some embodiments, as shown in FIG. 19A, the suction port 2112 can be positioned, at least partially, along an exterior of the assembly. However, in other embodiments, the port 2112 and/or corresponding passage (e.g., conduit) to with which the port is placed in fluid communication can extend, at least partially, along an interior of the assembly. For example, in some arrangements, the port and/or the corresponding passage can extend, at least in part, along the interior of the assembly, as desired or required.

As discussed with reference to other embodiments herein, the distal end of the assembly 2000 (e.g., the distal end of the handpiece portion 2110, the cartridge or other container 2040, a separate tip and/or any other component or portion) can include a peripheral lip or edge that is configured to contact the subject's skin. In some embodiments, such a lip and/or other periphery can help establish a seal with the adjacent tissue surface to ensure that, when a vacuum or suction source is activated, the targeted skin surface is engaged by the lip and/or other periphery. In some arrangements, this facilitates the delivery of fluids to the tip and removal of spend fluids and/or other debris (e.g., exfoliated skin) away from the tip.

Figure 20A:
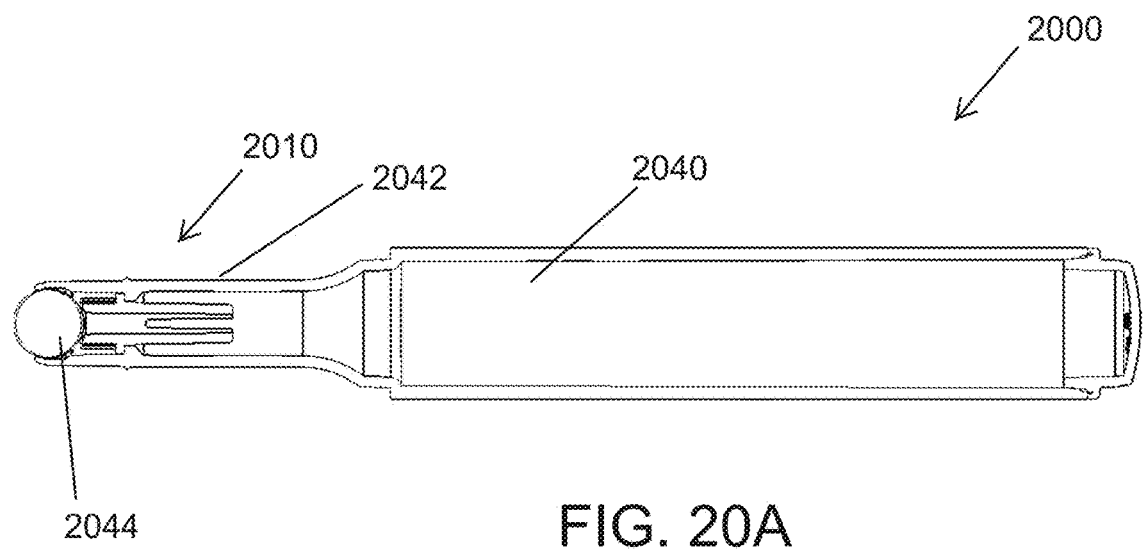
FIGS. 20A and 20B illustrate different cross-sectional views of the assembly of FIGS. 19A and 19B.
Figure 20B:
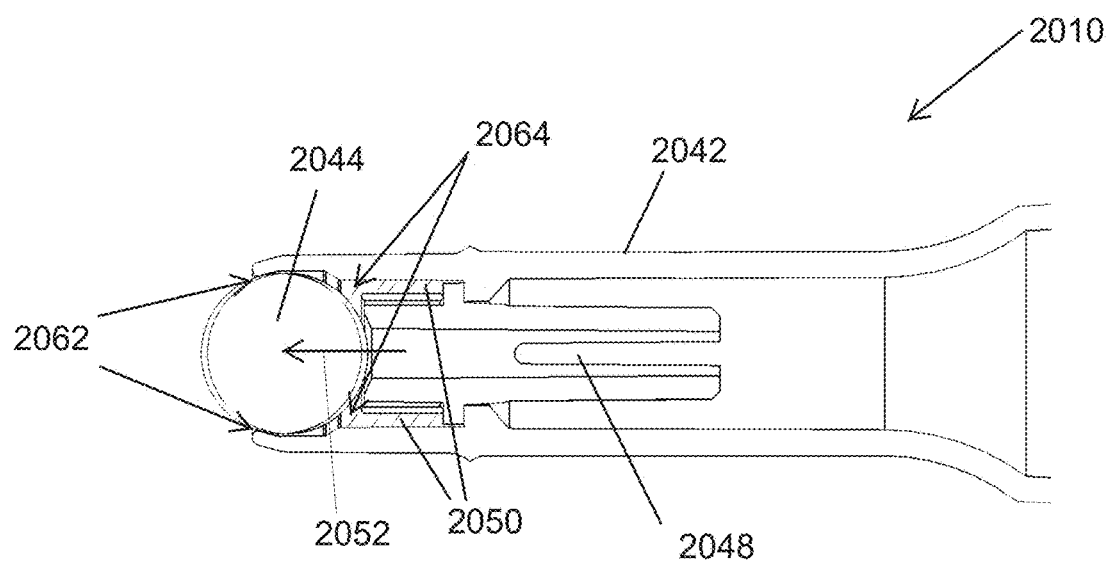

FIGS. 20A and 20B illustrate different longitudinal cross-sectional views of the assembly depicted in FIGS. 19A and 19B. As shown, the distal end of the container (e.g., a cartridge, a handpiece assembly, a tip, etc.) that includes the rollerball or other fluid delivery member (e.g., absorptive member, a wicking member, etc.) 2044. As shown, the distal end 2042 of the assembly 2000 can be tapered and/or otherwise include a reduced diameter or cross-sectional dimension, as desired or required. For example, in some embodiments, the distal end 2010 of the assembly 2000 along or near which the rollerball or other fluid delivery member (e.g., absorptive member, a wicking member, etc.) 2044 is positioned or otherwise located can include a diameter or other cross-sectional dimension that is 20% to 70% (e.g., 20-30, 30-40, 40-50, 50-60, 60-70%, ranges between the foregoing, etc.) smaller than adjacent portions of the assembly.

With continued reference to FIGS. 20A and 20B, the assembly 2000 can comprise a distal end 2010 that includes a tapered portion 2042. As shown, a rollerball or other fluid delivery member 2044 can be positioned along the distal end of the tapered portion 2042 and/or other portion of the distal end of the assembly 2000, as desired or required. As with other embodiment disclosed herein, the rollerball or other fluid delivery member 2044 can be in fluid communication with a main portion of the reservoir or compartment that contains fluid via one or more passageways 2048 along the tapered distal end 2042. In some configurations, the rollerball and/or other member (e.g., wicking member, porous member, etc.) 2062 can be resiliently biased distally using one or more springs and/or other resilient members or portions 2050. Such a configuration can be implemented in any of the embodiments disclosed herein or variations thereof.

Thus, according to some embodiments, the rollerball or other member 2044 is resiliently biased in a distal orientation. In such configurations, the rollerball or other fluid delivery member 2044 is normally configured to form a seal 2062. As a result, in such a configuration, fluids and/or other materials (e.g., contained within a cartridge and/or otherwise in fluid communication with the rollerball or the fluid delivery member 2044) are prevented from exiting past the rollerball or other fluid delivery member 2044. In some embodiments, pressing or otherwise moving the rollerball and/or other fluid delivery member 2044 (e.g., wicking member, porous member, etc.) inwardly (e.g., against the force created by the spring 2050 or other biasing or resilient member) can create clearance between the rollerball or other member 2044 and the adjacent housing, thereby allowing fluid to flow around the rollerball or other member toward the distal end of the assembly 2000.

In some embodiments, however, if sufficient force is imparted upon the rollerball or other assembly 2044, the rollerball or other assembly 2044 can abut against a distal surface 2064 of the housing and/or other portion of the assembly to prevent further fluids and/or other materials from exiting toward the distal end of the assembly. Thus, in some embodiments, one or more resilient members (e.g., springs) 2050 can help regulate the passage of fluid from a reservoir (e.g., from within a cartridge or other portion of the assembly) to the tip of the assembly 2000, as desired or required. In some embodiments, the force that is applied against the spring or other resilient member 2050 regulates the amount of flow (e.g., flowrate) that moves past the rollerball and/or another fluid delivery member 2044 located along eth distal end of the assembly 2000. Such a configuration can be applied to any of the embodiments disclosed herein. In some embodiments, moving the rollerball and/or any other distal member 2044 too far against the biasing force may cause the rollerball or the member to seat against a proximal portion 2064 that will once again prevent flow from to the distal end of the assembly. Thus, in some embodiments, there exists a range within which the rollerball or other resiliently-biased member 2044 can be moved in order to regulate flow to the distal end of the assembly 2000.

For any of the embodiments disclosed herein, a cartridge or other fluid source configured to be used in an assembly (e.g., to couple to a handpiece), the cartridge can include two or more compartments that are fluidly isolated from one another. For example, in some arrangements, a cartridge includes two or three chambers, each of which is configured to store a different serum and/or treatment material to be used during a specific treatment procedure. In some embodiments, such a multi-compartment cartridge or other fluid source is separated by walls, baffles or other members or features. In some embodiments, a user can choose between the various compartments of the cartridge (and thus, the various serums and/or other materials to be delivered to the subject's skin surface) using one or more selection features, methods or devices. For example, the cartridge, handpiece, tip and/or other portion of the assembly can include one or more controllers (e.g., switches, levers, knobs, etc.) that permit a user to select the specific compartment of the cartridge from which fluids and/or other materials will be transferred to the subject's skin. In other embodiments, the orientation of the cartridge within the handpiece dictates which compartment will be in fluid communication with the assembly's internal passages and the tip. For example, the rotational or angular orientation of the cartridge relative to the handpiece can determine which compartment of the cartridge will be accessed by the rollerball.

In any of the assembly embodiments disclosed herein or variations thereof, the tip can be placed in fluid communication with a fluid manifold system. Thus, one or more fluids from such a manifold system or station can be selectively delivered to the assembly. Accordingly, in some embodiments, a dummy cartridge or a simple fluid conduit can be used (e.g. instead of a filled cartridge) to interface with such a manifold system or station.

According to certain embodiments, a cartridge or other container is placed in fluid communication with a manifold system that may comprise a plurality of individual fluid conduits. In turn, one or more of these fluid conduits can be in fluid communication with a separate container. For example, in some embodiments, such fluid conduits can be in fluid communication with containers of a tower system. In one embodiment, the individual fluid lines are in fluid communication with a main fluid conduit, which connects to a nozzle along a proximal end of a cartridge or other container secured within the handpiece. One or more of the fluid conduits can comprise a valve or other flow control device or feature to selectively regulate the transfer of fluids and/or other materials to the assembly. In the some arrangements, the manifold system comprises a total of four fluid branches. However, a system can comprise more or fewer fluid branches (e.g., 1, 2, 3, 4, 5, 6, 7, 8, more than 8, etc.), as desired or required by a particular application or use. Additional details regarding a manifold system or tower are provided in U.S. patent application Ser. No. 11/392,348, filed on Mar. 29, 2006 and issued as U.S. Pat. No. 8,048,089 on Nov. 1, 2011, and PCT Application No. PCT/US2014/024992, filed on Mar. 12, 2014 and published as WO 2014/151104 on Sep. 25, 2014, the entireties of both of which are hereby incorporated by reference herein.

The systems, apparatuses, devices and/or other articles disclosed herein may be formed through any suitable means. The various methods and techniques described above provide a number of ways to carry out the inventions. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "providing" include "instructing providing." The ranges disclosed herein also encompass any and all overlap, subranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A skin treatment system comprising:
a handpiece assembly comprising a longitudinal axis, an interior portion, a proximal end and a distal end, the proximal end extending to a proximal-most location along the longitudinal axis, the handpiece assembly comprising a suction port extending along an exterior of the handpiece assembly, wherein the handpiece assembly comprises a peripheral lip along the distal end of the handpiece assembly;
a cartridge configured to releasably secure to the handpiece assembly, the cartridge comprising an interior chamber configured to contain a treatment fluid;
a rollerball positioned along a distal end of the cartridge, wherein the rollerball is configured to be in fluid communication with the interior of the cartridge; and
a vacuum source;
wherein the cartridge is configured to be positioned through the interior portion of the handpiece assembly to removably secure the cartridge to the handpiece assembly, wherein the rollerball extends distally past the peripheral lip of the handpiece assembly when the cartridge is secured to the handpiece assembly, and
wherein, when the cartridge is secured to the handpiece assembly, a proximal portion of the cartridge is proximal of the proximal-most location of the handpiece assembly and the suction port, and the cartridge and the handpiece assembly form an exterior surface that can be grasped and manipulated during use;
wherein the rollerball is configured to be surrounded by the peripheral lip of the handpiece assembly when the cartridge is secured to the handpiece assembly;
wherein the rollerball is configured to rotate to facilitate a transfer of the treatment fluid from the interior chamber of the cartridge to the rollerball; and
wherein the suction port is configured to be placed in fluid communication with the vacuum source to generate a suction along the distal end of the handpiece assembly when the vacuum source is activated; and
wherein, during use, the handpiece assembly is configured such that the suction along the distal end of the handpiece assembly is maintained as the cartridge is slidably separated relative to the handpiece assembly.

2. The system of claim 1, wherein the cartridge is configured to be separated from the handpiece assembly and provided to a subject being treated to permit the subject to apply the treatment fluid to skin tissue.

3. The system of claim 1, wherein the cartridge is disposable.

4. The system of claim 1, wherein the cartridge is reusable.

5. The system of claim 1, wherein the cartridge is configured to be selectively opened to access to the interior chamber.

6. The system of claim 1, wherein the cartridge is configured to remain sealed at all times.

7. The system of claim 1, wherein the cartridge is configured to contain an acid.

8. The system of claim 1, further comprising a cap configured to be positioned along the distal end of the cartridge between uses of the cartridge.

9. The system of claim 1, wherein the cartridge is configured to help maintain the treatment fluid within the interior chamber immediately adjacent the rollerball.

10. The system of claim 9, wherein one or more vanes are positioned adjacent the rollerball to help maintain the treatment fluid immediately adjacent the rollerball.

11. The system of claim 9, wherein a wicking or other porous member is positioned adjacent the rollerball to help maintain the treatment fluid immediately adjacent the rollerball.

12. The system of claim 1, wherein the peripheral lip is configured to contact a subject's skin tissue and form a seal along said skin tissue during use.

13. A skin treatment system comprising:
a handpiece assembly comprising a suction port extending along an exterior of the handpiece assembly, the handpiece assembly comprising a longitudinal axis, a proximal end, an interior portion and a peripheral lip along a distal end, the proximal end extending to a proximal-most location along the longitudinal axis;
a cartridge configured to releasably secure to the handpiece assembly, the cartridge comprising an interior chamber configured to contain a treatment fluid, wherein, when the cartridge is secured to the handpiece assembly, a proximal portion of the cartridge is proximal of the proximal end of the handpiece assembly, and the cartridge and the handpiece assembly form an exterior surface that can be grasped and manipulated during use; and a rollerball positioned along a distal end of the cartridge, wherein the rollerball is configured to be in fluid communication with the interior of the cartridge;

wherein the rollerball extends distally past the peripheral lip of the handpiece assembly when the cartridge is removably secured to the handpiece assembly, wherein the cartridge is configured to be positioned through the interior portion of the handpiece assembly to removably secure the cartridge to the handpiece assembly;

wherein a proximal portion of the cartridge is proximal of the proximal-most location of the handpiece assembly and the suction port, and wherein the cartridge and the handpiece assembly form an exterior surface that can be grasped and manipulated during use;

wherein the rollerball is configured to be surrounded by the peripheral lip of the handpiece assembly when the cartridge is secured to the handpiece assembly; and wherein the suction port is configured to be placed in fluid communication with the vacuum source.

14. The system of claim 13, wherein the cartridge is configured to be separated from the handpiece assembly and provided to a subject being treated to permit the subject to apply the treatment fluid to skin tissue.

15. The system of claim 13, wherein the cartridge is disposable or reusable.

16. The system of claim 13, further comprising a cap configured to be positioned along the distal end of the cartridge between uses of the cartridge.

17. The system of claim 13, wherein the cartridge is configured to help maintain the treatment fluid within the interior chamber immediately adjacent the rollerball.

18. The system of claim 17, wherein one or more vanes are positioned adjacent the rollerball to help maintain the treatment fluid immediately adjacent the rollerball.

19. The system of claim 17, wherein a wicking or other porous member is positioned adjacent the rollerball to help maintain the treatment fluid immediately adjacent the rollerball.

20. The system of claim 13, wherein the peripheral lip is configured to contact a subject's skin tissue and form a seal along said skin tissue during use.

* * * * *